United States Patent [19]

Baum et al.

[11] Patent Number: 4,659,360

[45] Date of Patent: Apr. 21, 1987

[54] PLANT GROWTH AND DEVELOPMENT MODIFICATION USING BENZOXAZOLE DERIVATIVES

[75] Inventors: Jonathan S. Baum, Pennington; Tsong M. Chen, Princeton Junction, both of N.J.

[73] Assignee: FMC Corporation, Philadelphia, Pa.

[21] Appl. No.: 676,972

[22] Filed: Nov. 30, 1984

[51] Int. Cl.[4] .................... A01N 43/12; C07D 263/08

[52] U.S. Cl. .......................................... 71/88; 548/224

[58] Field of Search ............................ 548/224; 71/88

[56] References Cited

U.S. PATENT DOCUMENTS

| | | | |
|---|---|---|---|
| 3,551,443 | 12/1970 | Dwennenburger et al. | 548/224 |
| 3,876,791 | 4/1975 | Hubbard et al. | 514/367 |
| 3,947,582 | 3/1976 | Shen et al. | 514/375 |
| 4,174,321 | 11/1979 | Wang et al. | 548/224 |
| 4,271,307 | 6/1981 | Irick et al. | 548/224 |
| 4,319,026 | 3/1982 | Hedrich et al. | 542/419 |

FOREIGN PATENT DOCUMENTS

| | | | |
|---|---|---|---|
| 1090497 | 11/1967 | United Kingdom . | |
| 1131405 | 10/1968 | United Kingdom | 548/224 |
| 1156800 | 7/1969 | United Kingdom | 548/224 |

OTHER PUBLICATIONS

Hirikir et al., "Film for Cultivation of Beans", Chem. Abst. 93:27450(d), (1980).
Shomansurou, S., "Natural Growth Regulators of Bean, . . . " Chem. Abst. 96:30857j.
Brown et al., *Pestic Sci.*, 4, 473 (1973).
Bystrov et al., *J. Gen. Chem. USSR*, 963 (1968).
*Chem. Abstr.*, 101, 177262s (1984).
Chem. Abstr., 51, 373c (1957).
Katekar, *Phytochem.*, 15, 1421 (1976).
Katekar et al., *Phytochem.*, 20, 2465 (1981).
Katekar et al., *Plant Physiol.*, 60, 826 (1977).
Katekar et al., *Plant Physiol.*, 66, 1190 (1980).
Wada et al., *J. Med. Chem.*, 16, 930 (1973).

*Primary Examiner*—Donald G. Daus
*Assistant Examiner*—G. Hendricks
*Attorney, Agent, or Firm*—H. R. Ertelt; R. L. Hansen

[57] ABSTRACT

Benzoxazole compounds of the following structural formula modify the growth and development of plants:

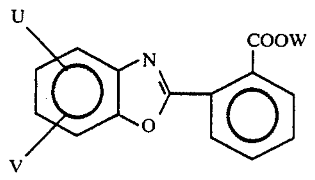

wherein

U is selected from -hydrogen, -halogen, -lower alkyl, -lower alkenyl, -phenylmethyl, -phenyl, -nitro, -hydroxycarbonyl, -phenylcarbonyl, -halophenylcarbonyl, -phenylthio, -phenylsulfoxy, -phenylsulfonyl, and a substituent of the formula

—OZ in which Z is -aryl or -aryl carring 1 or 2 substituents independently selected from -halogen, -lower alkyl, -lower haloalkyl, -lower alkoxy, -acetamido, and -phenyl;

V is selected from -hydrogen, -halogen and -lower alkyl, or U and V taken together are $-C_4H_4-$ joining adjacent ring positions; and W is selected from -hydrogen, -lower alkyl optionally substituted with -alkoxycarbonyl, and an agriculturally acceptable cation.

18 Claims, No Drawings

PLANT GROWTH AND DEVELOPMENT MODIFICATION USING BENZOXAZOLE DERIVATIVES

This invention is in the field of organic chemical compounds; more specifically, it pertains to novel 2-(2-oxycarbonylphenyl)benzoxazoles, processes and intermediates thereto, plant growth and development modifying compositions containing 2-(2-oxycarbonylphenyl)benzoxazoles, and to the use of 2-(2-oxycarbonylphenyl)benzoxazoles for modifying the growth and development of plants.

A number of organic chemical compounds modify the growth and development of plants. Application of an organic chemical to plants may cause death of the plants. Such chemicals are referred to as herbicides. Although broad spectrum herbicides have recognized utility, herbicidal activity is often more desirable if it is selective, sparing crops, but killing weeds. Occasionally organic compounds are discovered which are not simply nutrients, but, when applied in the recommended manner, selectively modify the normal growth and development of plants and do not kill them.

Beneficial effects from such modification include increasing the yield of fruit, seeds, fiber, or other plant products. Another beneficial effect may be an increase in the nutritional value of food products derived from the plants. It is a beneficial effect of some compounds to facilitate harvesting the plant product. Yet another beneficial effect in certain cases is an increase in the products's storage life. Such chemical compounds, beneficial to plants in small amounts, are referred to as plant growth regulators. Plant growth and development modifications leading to such effects include, but are not limited to: root initiation; set, development, ripening and abscission of fruits; plant size and shape; suppression of lodging; control of axillary buds and lateral shoots; metabolism regulation, including senescence; breaking or enforcing dormancy in seeds, buds, and storage organs; promotion or delay of flowering; defoliation; desiccation; and growth promotion under stress.

Sometimes an organic chemical compound displays plant growth and development regulation characterized by both herbicidal activity and plant growth regulator activity depending upon the species of plant, the time of application in the plant growth cycle, the site of application, and the amount of chemical employed, i.e., the application rate.

The plant growth and development modifying 2-(2-oxycarbonylphenyl)benzoxazoles of this invention are in the latter category. In general, they can be made to behave as either herbicides or plant growth regulators depending upon the way they are used.

A 2-(2-oxycarbonylphenyl)benzoxazole is a condensed ring heteroaromatic compound containing the following structural unit:

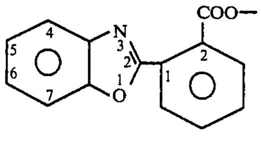

The ring atom numbering scheme is shown for convenient reference.

Both 2-(3-carboxyphenyl)benzoxazole and the (4-carboxyphenyl)isomer are known compounds, as are the corresponding methyl esters; see *J. Gen. Chem. USSR*, 963 (1968). U.S. Pat. No. 3,947,582 discloses related benzoxazole phenylacetic acids and their pharmaceutical utility. The herbicidal activity of certain 2-phenylbenzoxazoles is disclosed in GB 1,090,497, and U.S. Pat. No. 4,319,026 describes 2-substituted benzoxazole plant growth regulators.

According to the present invention 2-(2-oxycarbonylphenyl)benzoxazoles of the following formula have been found to modify the growth and development of plants:

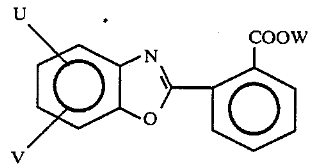

wherein

U is selected from -hydrogen, -halogen, -lower alkyl, -lower alkenyl, -phenylmethyl, -phenyl, -nitro, -hydroxycarbonyl, -phenylcarbonyl, -halophenylcarbonyl, -phenylthio, -phenylsulfoxy, -phenylsulfonyl, and a substituent of the formula

—OZ in which Z is -aryl or -aryl carrying 1 or 2 substituents independently selected from -halogen, -lower alkyl, -lower haloalkyl, -lower alkoxy, -acetamido, and -phenyl;

V is selected from -hydrogen, -halogen, and -lower alkyl, or U and V taken together are $—C_4H_4—$ joining adjacent ring positions; and W is selected from -hydrogen, -lower alkyl optionally substituted with -alkoxycarbonyl, and an agriculturally acceptable cation.

In the aforesaid description and wherever employed in this application the terms "halogen" or "halo" mean fluorine, chlorine and bromine. Similarly, the terms "lower alkyl" and "lower alkenyl" mean a straight or branched chain containing 1 to 6, preferably 1 to 4, carbon atoms, and the term "lower alkoxy" contemplates bonded to oxygen a straight or branched chain containing 1 to 6, preferably 1 to 4, carbon atoms. The terms "haloalkyl," "halophenyl," or the like mean one or more hydrogen atoms has been replaced by halogen. The term "aryl" includes phenyl, naphthyl, heterocyclics such as 2,2-dimethylbenzofuranyl, and equivalents thereof. "Agriculturally acceptable cations" include, but are not limited to, alkali and alkaline earth metals such as sodium, potassium, calcium, lithium, and magnesium, or other metals such as copper, zinc, aluminum or iron; ammonium, mono-, di-, or tri-substituted ammonium, such as methylammonium, 1-methylethylammonium, diethylammonium, triethylammonium, hexylammonium, dodecylammonium, ethanolammonium, diethanolammonium, hexanolammonium, or dodecanolammonium.

Many of the 2-(2-oxycarbonylphenyl)benzoxazoles are new compounds, constituting one aspect of this invention. However, the instant invention also includes plant growth and development modifying compositions comprising in admixture with an agriculturally acceptable carrier a plant growth and development modifying effective amount of at least one of the aforesaid 2-(2-oxycarbonylphenyl)benzoxazoles. Furthermore, the invention includes as another aspect the method of modifying the growth and development of plants which comprises applying to the locus where such modification is desired a plant growth and development modifying effective amount of at least one 2-(2-oxycarbonylphenyl)benzoxazole within the aforesaid description.

Among the aforesaid 2-(2-oxycarbonylphenyl)benzoxazoles the most interesting from the standpoint of overall activity are generally the acids and salts, i.e., compounds in which W is either -hydrogen or an agriculturally acceptable cation. Within this set it is preferred that V be -hydrogen and that U be a 5-, 6- or 7-substituent, especially a 5- or 6-substituent. Other attractive compounds are those in which U and V together are $-C_4H_4-$ joining either the 4- and 5-positions or the 5- and 6-positions.

In those compounds in which V is -hydrogen the most attractive properties generally are seen in those compounds wherein U is -alkyl (especially -methyl), -phenyl, -phenylthio, -phenylsulfoxy, -phenylsulfonyl, -phenylcarbonyl, -halophenylcarbonyl, and especially -OZ. Preferred substituents Z include -phenyl, especially phenyl carrying -halogen, haloalkyl, or -acetamido substitution; -naphthyl; and 2,2-dimethyl-7-benzofuranyl.

If the 2-(2-oxycarbonylphenyl)benzoxazoles are to be used as herbicides, attractive specific compounds include 2-(2-carboxyphenyl)-6-phenoxybenzoxazole; 2-(2-carboxyphenyl)-6-(4-chlorophenoxy)benzoxazole; 2-(2-carboxyphenyl)-6-(2,4-dichlorophenoxy)benzoxazole; 2-(2-carboxyphenyl)-6-(2-chloro-4-trifluoromethylphenoxy)benzoxazole; and agriculturally acceptable cation salts of 2-(2-carboxyphenyl)-6-(2,4-dichlorophenoxy)benzoxazole, 2-(2-carboxyphenyl)-6-(2-chloro-4-trifluoromethyl phenoxy)benzoxazole, and 2-(2-carboxyphenyl)-6-(4-methylphenoxy)benzoxazole. Among the aforesaid herbicidal compounds, an agriculturally acceptable cation salt of 2-(2-carboxyphenyl)-6-(2-chloro-4-trifluoromethylphenoxy)benzoxazole is preferred for both preemergence and postemergence application.

With regard to plant growth regulation, the compounds in which W is -hydrogen or an agriculturally acceptable cation are substantially equivalent. Noteworthy plant growth regulating 2-(2-oxycarbonylphenyl)benzoxazoles include 2-(2-carboxyphenyl)-6-phenylbenzoxazole; 2-(2-carboxyphenyl)-5-phenoxybenzoxazole; 2-(2-carboxyphenyl)-6-phenoxybenzoxazole; 2-(2-carboxyphenyl)-6-(2-chloro-4-trifluoromethylphenoxy)benzoxazole; 2-(2-carboxyphenyl)-6-(4-methylphenoxy)benzoxazole; 2-(2-carboxyphenyl)-6-(phenylsulfinyl)benzoxazole; 2-(2-carboxyphenyl)-6-(4-acetamidophenoxy)benzoxazole; 2-(2-carboxyphenyl)-6-(2,2-dimethyl-7-benzofuranoxy)benzoxazole; 2-(2-carboxyphenyl)-naphtho[2,1-d]oxazole; 2-(2-carbomethoxyphenyl)-6-phenoxybenzoxazole; 2-(2-carbomethoxyphenyl)-6-(α-naphthoxy)benzoxazole; and agriculturally acceptable cation salts of 2-(2-carboxyphenyl)-6-(2-chloro-4-trifluoromethylphenoxy)benzoxazole.

Among the aforesaid plant growth regulators 2-(2-carboxyphenyl)-6-phenylbenzoxazole, 2-(2-carboxyphenyl)-6-(2-chloro-4-trifluoromethylphenoxy)benzoxazole, and especially 2-(2-carboxyphenyl)-5-phenoxybenzoxazole display promising activity.

The 2-(2-oxycarbonylphenyl)benzoxazoles of this invention can be prepared by adaptations of synthesis techniques described in the literature. The following general technique is employed:

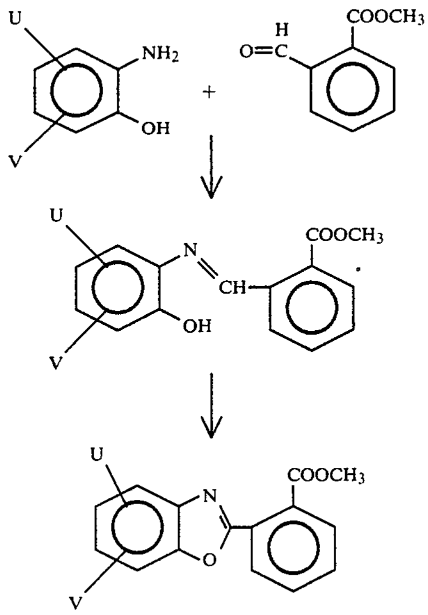

Those compounds in which W is other than methyl are readily derived from the esters by known methods. The starting 2-carbomethoxybenzaldehyde can be prepared by the method of Brown and Sargent, *J. Chem. Soc.* (C), 1818 (1969), while the appropriately substituted 2-aminophenol is readily derived from the corresponding 2-nitrophenol, e.g., by catalytic hydrogenation.

The condensation of 2-carbomethoxybenzaldehyde with the appropriately substituted 2-aminophenol, producing a Schiff base, as well as cyclization of the latter, can be effected by the methods of Stephens and Bower, *J. Chem. Soc.*, 2971 (1949). These processes will be clarified upon reference to the following Example.

EXAMPLE 58

2-(2-Carbomethoxyphenyl)-6-(2-chloro-4-trifluoromethylphenoxy)benzoxazole

A solution of 2.3 grams (0.0008 mole) 2-amino-5-((2-chloro-4-trifluoromethylphenoxy)phenol in ethanol was heated on a steam bath, and 1.2 grams (0.008 mole) of o-carbomethoxybenzaldehyde in ethanol was added. The reaction mixture was then heated on the steam bath for an additional hour. The cooled reaction mixture was concentrated under reduced pressure to give 3.4 g of N-(o-carbomethoxybenzylidene)-2-hydroxy-4-(2-chloro-4-trifluoromethylphenoxy)aniline that solidified on standing; m.p. 82°-85° C.

To a stirred solution of 2.7 grams (0.006 mole) N-(o-carbomethoxybenzylidene)-2-hydroxy-4-(2-chloro-4-trifluoromethylphenoxy)aniline in 25 ml of chloroform was added portionwise 2.9 grams (0.007 mole) lead tetraacetate. The reaction mixture was stirred for an additional hour, then washed sequentially with three portions of water and an aqueous saturated sodium chloride solution. The organic layer was concentrated under reduced pressure to a residual oil. The oil was dissolved in methylene chloride and passed through a column of activated magnesium silicate. The appropriate fractions were combined and concentrated under reduced pressure to give 2.2 grams of 2-(o-carbomethoxyphenyl)-6-(2-chloro-4-trifluoromethylphenoxy)-benzoxazole as an oil. The nmr spectrum was consistent with the proposed structure.

Analysis: nmr (δ, $CHCl_3$): 3.87 (s, 3H); 6.93–8.23 (m, 10H).

Following is a list of other 2-(2-oxycarbonylphenyl)-benzoxazoles within the scope of this invention prepared by similar techniques, together with mp (°C.) where applicable.

| Example | |
|---|---|
| 1 | 2-(2-Carboxyphenyl)benzoxazole, mp 211–214. |
| 2 | 2-(2-Carboxyphenyl)-5-chlorobenzoxazole, mp 205–207. |
| 3 | 2-(2-Carboxyphenyl)-7-chlorobenzoxazole, mp 235–236. |
| 4 | 2-(2-Carboxyphenyl)-5,7-dichlorobenzoxazole, mp 199–202, dec. |
| 5 | 2-(2-Carboxyphenyl)-4-methylbenzoxazole, mp 155–156. |
| 6 | 2-(2-Carboxyphenyl)-5-methylbenzoxazole, mp 203–205. |
| 7 | 2-(2-Carboxyphenyl)-6-methylbenzoxazole, mp 243–246. |
| 8 | 2-(2-Carboxyphenyl)-7-methylbenzoxazole, mp 225–227. |
| 9 | 2-(2-Carboxyphenyl)-7-(2-methylpropyl)benzoxazole, mp 160–162. |
| 10 | 2-(2-Carboxyphenyl)-5-(1,1-dimethylethyl)benzoxazole, mp 68–73. |
| 11 | 2-(2-Carboxyphenyl)-7-(2-methyl-2-propenyl)benzoxazole, mp 147–150. |
| 12 | 2-(2-Carboxyphenyl)-5,7-dimethylbenzoxazole, mp 204–206. |
| 13 | 2-(2-Carboxyphenyl)-5-nitrobenzoxazole, mp 238–241. |
| 14 | 2-(2-Carboxyphenyl)-5-carboxybenzoxazole, mp 227, dec. |
| 15 | 2-(2-Carboxyphenyl)-5-phenylbenzoxazole, mp 171–179 |
| 16 | 2-(2-Carboxyphenyl)-6-phenylbenzoxazole, mp 205–206. |
| 17 | 2-(2-Carboxyphenyl)-7-phenylbenzoxazole, mp 238–240. |
| 18 | 2-(2-Carboxyphenyl)-5-phenoxybenzoxazole, mp 142–144. |
| 19 | 2-(2-Carboxyphenyl)-6-phenoxybenzoxazole, mp 154–155. |
| 20 | 2-(2-Carboxyphenyl)-6-(4-chlorophenoxy)benzoxazole, mp 148–149. |
| 21 | 2-(2-Carboxyphenyl)-6-(2,4-dichlorophenoxy)benzoxazole, mp 181–182. |
| 22 | 2-(2-Carboxyphenyl)-6-(3,4-dichlorophenoxy)benzoxazole, mp 174–176. |
| 23 | 2-(2-Carboxyphenyl)-6-(2-chloro-4-trifluoromethyl-phenoxy)benzoxazole, mp 175–176. |
| 24 | 2-(2-Carboxyphenyl)-6-(4-methylphenoxy)benzoxazole, mp 169–170. |
| 25 | 2-(2-Carboxyphenyl)-6-(4-methoxyphenoxy)benzoxazole, mp 159–160. |
| 26 | 2-(2-Carboxyphenyl)-6-(4-phenylphenoxy)benzoxazole, mp 198–200. |
| 27 | 2-(2-Carboxyphenyl)-6-(αnaphthoxy)benzoxazole, mp 162–164. |
| 28 | 2-(2-Carboxyphenyl)-6-(βnaphthoxy)benzoxazole, mp 154–155. |
| 29 | 2-(2-Carboxyphenyl)-6-phenylthiobenzoxazole, mp 146–147. |
| 30 | 2-(2-Carboxyphenyl)-6-(phenylsulfinyl)benzoxazole, mp 135–141. |
| 31 | 2-(2-Carboxyphenyl)-6-(phenylsulfonyl)benzoxazole, mp 201–203. |
| 32 | 2-(2-Carboxyphenyl)-5-benzoylbenzoxazole, mp 173–174. |
| 33 | 2-(2-Carboxyphenyl)-5-(4-chlorobenzoyl)benzoxazole, mp 165–168. |
| 34 | 2-(2-Carboxyphenyl)-naphtho[1,2-d]oxazole, mp 181–183. |
| 35 | 2-(2-Carboxyphenyl)-naphtho[2,3-d]oxazole, mp 196–198. |
| 36 | 2-(2-Carbomethoxyphenyl)benzoxazole, liquid. |
| 37 | 2-(2-Carbomethoxyphenyl)-5-chlorobenzoxazole, mp 76–80. |
| 38 | 2-(2-Carbomethoxyphenyl)-7-chlorobenzoxazole, mp 92–93. |
| 39 | 2-(2-Carbomethoxyphenyl)-5,7-dichlorobenzoxazole, mp 106–107. |
| 40 | 2-(2-Carbomethoxyphenyl)-4-methylbenzoxazole, liquid. |
| 41 | 2-(2-Carbomethoxyphenyl)-5-methylbenzoxazole, liquid. |
| 42 | 2-(2-Carbomethoxyphenyl)-6-methylbenzoxazole, liquid. |
| 43 | 2-(2-Carbomethoxyphenyl)-7-methylbenzoxazole, liquid. |
| 44 | 2-(2-Carbomethoxyphenyl)-7-(2-methylpropyl)benzoxazole, liquid. |
| 45 | 2-(2-Carbomethoxyphenyl)-5-(1,1-dimethylethyl)benzoxazole, liquid. |
| 46 | 2-(2-Carbomethoxyphenyl)-7-(2-methyl-2-propenyl)-benzoxazole, liquid. |
| 47 | 2-(2-Carbomethoxyphenyl)-5,7-dimethylbenzoxazole, |

-continued

| Example | |
|---|---|
| | liquid. |
| 48 | 2-(2-Carbomethoxyphenyl)-5-nitrobenzoxazole, mp 134–135. |
| 49 | 2-(2-Carbomethoxyphenyl)-5-carboxybenzoxazole, mp 201–202. |
| 50 | 2-(2-Carbomethoxyphenyl)-5-phenylbenzoxazole, liquid. |
| 51 | 2-(2-Carbomethoxyphenyl)-6-phenylbenzoxazole, mp 83–83. |
| 52 | 2-(2-Carbomethoxyphenyl)-7-phenylbenzoxazole, mp 92–95. |
| 53 | 2-(2-Carbomethoxyphenyl)-5-phenoxybenzoxazole, liquid. |
| 54 | 2-(2-Carbomethoxyphenyl)-6-phenoxybenzoxazole, liquid. |
| 55 | 2-(2-Carbomethoxyphenyl)-6-(4-chlorophenoxy)benzoxazole, liquid. |
| 56 | 2-(2-Carbomethoxyphenyl)-6-(2,4-dichlorophenoxy)benzoxazole, liquid. |
| 57 | 2-(2-Carbomethoxyphenyl)-6-(3,4-dichlorophenoxy)benzoxazole, mp 75–77. |
| 59 | 2-(2-Carbomethoxyphenyl)-6-(4-methylphenoxy)benzoxazole, liquid. |
| 60 | 2-(2-Carbomethoxyphenyl)-6-(4-methylphenoxy)benzoxazole, liquid. |
| 61 | 2-(2-Carbomethoxyphenyl)-6-(4-acetamidophenoxy)benzoxazole, mp 62–65. |
| 62 | 2-(2-Carbomethoxyphenyl)-6-(4-phenylphenoxy)benzoxazole, mp 112–114. |
| 63 | 2-(2-Carbomethoxyphenyl)-6-(α-naphthoxy)benzoxazole, liquid. |
| 64 | 2-(2-Carbomethoxyphenyl)-6-(β-naphthoxy)benzoxazole, mp 101–103. |
| 65 | 2-(2-Carbomethoxyphenyl)-6-phenylthiobenzoxazole, mp 79–80. |
| 66 | 2-(2-Carbomethoxyphenyl)-6-(phenylsulfinyl)benzoxazole, mp 119–120. |
| 67 | 2-(2-Carbomethoxyphenyl)-6-(phenylsulfonyl)benzoxazole, mp 140–141. |
| 68 | 2-(2-Carbomethoxyphenyl)-5-benzoylbenzoxazole, mp 115–116. |
| 69 | 2-(2-Carbomethoxyphenyl)-5-(4-chlorobenzoyl)benzoxazole mp 128–130. |
| 70 | 2-(2-Carbomethoxyphenyl)-naphtho[1,2-d]oxazole, liquid. |
| 71 | 2-(2-Carbomethoxyphenyl)-naphtho[2,3-d]oxazole, mp 133–134. |
| 72 | 2-(2-Carbomethoxyphenyl)benzoxazole, 1-methylethylamine salt, mp 128–132. |
| 73 | 2-(2-Carboxyphenyl)-5-chlorobenzoxazole, 1-methylethylamine salt, mp 146–150. |
| 74 | 2-(2-Carboxyphenyl)-7-chlorobenzoxazole, 1-methylethylamine salt, mp 164–166. |
| 75 | 2-(2-Carboxyphenyl)-5,7-dichlorobenzoxazole, 1-methylethylamine salt, mp 111–116. |
| 76 | 2-(2-Carboxyphenyl)-4-methylbenzoxazole, 1-methylethylamine salt, mp 161–163. |
| 77 | 2-(2-Carboxyphenyl)-5-methylbenzoxazole, 1-methylethylamine salt, mp 150, dec. |
| 78 | 2-(2-Carboxyphenyl)-6-methylbenzoxazole, 1-methylethylamine salt, mp 149–151. |
| 79 | 2-(2-Carboxyphenyl)-7-methylbenzoxazole, 1-methylethylamine salt, mp 164–166. |
| 80 | 2-(2-Carbomethoxyphenyl)-5-(1,1-dimethylethyl)benzoxazole, 1-methylethylamine salt, mp 70–75, dec. |
| 81 | 2-(2-Carboxyphenyl)-5-nitrobenzoxazole, 1-methylethylamine salt, mp 110, dec. |
| 82 | 2-(2-Carboxyphenyl)-5-phenylbenzoxazole, 1-methylethylamine salt, mp 170–176, dec. |
| 83 | 2-(2-Carboxyphenyl)-6-phenylbenzoxazole, 1-methylethylamine salt, mp. 176–179. |
| 84 | 2-(2-Carboxyphenyl)-7-phenylbenzoxazole, 1-methylethylamine salt, mp 192–193. |
| 85 | 2-(2-Carboxyphenyl)-5-phenoxybenzoxazole, 1-methylethylamine salt, mp 118–120. |
| 86 | 2-(2-Carboxyphenyl)-6-(2,4-dichlorophenoxy)benzoxazole, 1-methylethylamine salt, mp 70–73, hygroscopic. |
| 87 | 2-(2-Carboxyphenyl)-6-(3,4-dichlorophenoxy)benzoxazole, 1-methylethylamine salt, mp 129–130. |
| 88 | 2-(2-Carboxyphenyl)-6-(2-chloro-4-trifluoromethylphenoxy)benzoxazole, 1-methylethylamine salt, mp 69–71. |

-continued

| Example | |
|---|---|
| 89 | 2-(2-Carboxyphenyl)-6-(4-methylphenoxy)benzoxazole, 1-methylethylamine salt, mp 175–178. |
| 90 | 2-(2-Carboxyphenyl)-6-(4-methylphenoxy)benzoxazole, 1-methylethylamine salt, mp 154–155. |
| 91 | 2-(2-Carboxyphenyl)-6-(4-phenylphenoxy)benzoxazole, 1-methylethylamine salt, mp 171–174. |
| 92 | 2-(2-Carboxyphenyl)-6-(α-naphthoxy)benzoxazole, 1-methylethylamine salt, mp 174–177. |
| 93 | 2-(2-Carboxyphenyl)-6-(β-naphthoxy)benzoxazole, 1-methylethylamine salt, mp 163–166. |
| 94 | 2-(2-Carboxyphenyl)-6-phenylthiobenzoxazole, 1-methylethylamine salt, mp. 128–129. |
| 95 | 2-(2-Carboxyphenyl)-naphtho[1,2-d]oxazole, 1-methylethylamine salt, mp 170–173. |
| 96 | 2-(2-Carboxyphenyl)-naphtho[2,3-d]oxazole, 1-methylethylamine salt, mp 177–181. |
| 97 | 2-(2-Carboxyphenyl)-5-phenylmethylbenzoxazole, mp 50–53. |
| 98 | 2-(2-Carboxyphenyl)-6-(4-acetamidophenoxy)benzoxazole, mp 208–209. |
| 99 | 2-(2-Carbomethoxyphenyl)-5-phenylmethylbenzoxazole, liquid. |
| 100 | 2-(2-Carbomethoxyphenyl)-6-(2,2-dimethyl-7-benzofuranoxy)benzoxazole, liquid. |
| 101 | 2-(2-Carboxyphenyl)-6-(2,2-dimethyl-7-benzofuranoxy)benzoxazole, mp 235–237. |
| 102 | 2-(Carbo-[2-(1-ethoxypropanoyl)oxy]phenyl)-5-phenylbenzoxazole, liquid. |
| 103 | [ 2-(1-ethoxypropanoyl)oxy]phenyl)-5-methylbenzoxazole, mp 95–97. |
| 104 | 2-(Carbo-[2-(1-ethoxypropanoyl)oxy]phenyl)-6-(4-methylphenoxy)benzoxazole, liquid. |
| 105 | 2-(2-Carbomethoxyphenyl)-5-(4-methoxyphenoxy)benzoxazole, liquid. |
| 106 | 2-(2-Carboxyphenyl)-5-(4-methoxyphenoxy)benzoxazole, mp 214–215. |
| 107 | 2-(2-Carbomethoxyphenyl)-naptho[2,1-d]oxazole, liquid. |
| 108 | 2-(2-Carboxyphenyl)-naptho[2,1-d]oxazole, mp 228–230. |
| 109 | 2-(2-Carbomethoxyphenyl)-5-(2-chloro-4-trifluoromethylphenoxy)benzoxazole, liquid. |
| 110 | 2-(2-Carboxyphenyl)-5-(2-chloro-4-trifluoromethylphenoxy)benzoxazole, mp 179–180. |

In the normal use of the aforesaid 2-(2-oxycarbonylphenyl)benzoxazole plant growth and development modifiers, the active compounds usually will be not employed free from admixture or dilution, but ordinarily will be used in a suitable formulated agricultural composition compatible with the method of application and comprising a plant growth and development modifying effective amount of at least one of said active compounds. Said benzoxazoles, like most pesticidal agents, may be blended with the agriculturally acceptable surface-active agents and carriers normally employed for facilitating the dispersion of active ingredients, recognizing the accepted fact that the formulation and mode of application of a plant growth and development modifier may affect the activity of the material. The present active compounds may be applied, for example, as sprays, dusts, or granules to the area where plant growth and development modification is desired, the type of application varying of course with the plant and the environment. Thus, the benzoxazole compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for said active compounds. The granule particles are relatively large, a diameter of about 400–2500 microns typically. The particles are either impregnated with the active compound from solution or coated with the compound, adhesive sometimes being employed. Granules generally contain 0.05–20% by weight, preferably 0.5–5%, active ingredient as the plant growth and development modifying effective amount. A typical granular formulation employed for evaluation purposes contains 95% attapulgite clay (24/48 mesh) and 5% 2-(2-carboxyphenyl)-6-phenylbenzoxazole.

Dusts are admixtures of said active compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the plant growth and development modifier. These finely divided solids have an average particle size of less than about 50 microns. A typical dust formulation useful for modifying the growth and development of plants contains by weight 5 parts 2-(2-carboxyphenyl)-6-phenylbenzoxazole and 95 parts talc.

The benzoxazole compounds of the present invention may be made into liquid concentrates by dissolution or emulsification in suitable liquids and into solid concentrates by admixture with talc, clays, and other known solid carriers used in the pesticide art. The concentrates are compositions containing, as a plant growth and development modifying effective amount, about 5–50% the benzoxazole by weight and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts. Typical carriers for solid concentrates (also called wettable powders) include fuller's earth, clays, silicas, and other highly absorbent, readily wetted inorganic diluents.

Manufacturing concentrates are useful for shipping low melting products of this invention. Such concentrates are prepared by melting the solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in agricultural formulations include, for example, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the plant growth regulator composition.

Other useful formulations include simple solutions of the active ingredient in a solvent in which it is completely soluble at the desired concentration, such as acetone or other organic solvents.

A plant growth and development modifying effective amount of said benzoxazole in a plant growth and development modifying composition diluted for application is normally in the range of about 0.004% to about 5% by weight. Many variations of spraying and dusting compositions known in the art may be used by substituting said plant growth and development modifying compounds of this invention into compositions known or apparent to the art. The plant growth and development modifying compositions of this invention may be formulated with other active ingredients, including insecticides, nematicides, acaricides, fungicides, other herbicides or plant growth regulators, fertilizers, etc.

In using the compositions to modify plant growth and development according to the method of this invention, it is only necessary that a plant growth and development modifying, or herbicidally, or plant growth regulant, effective amount of at least one of said benzoxazoles, depending on the objective, be applied to the locus where such modification, or control, or regulation is desired, generally a soil locus where agricultural crops are grown and either before or, preferably, after the plants have emerged. Liquid plant growth regulator compositions may be incorporated into the soil, applied to the soil as a drench, or sprayed on the foliage of growing plants. Solid compositions may be applied by broadcasting or in bands. For most applications, a plant growth and development modifying, or herbicidally, or plant growth regulant, effective amount will be about 0.005 to 8 kg, preferably 0.01 to 2 kg, per hectare.

The plant growth and development modifiers of this invention were investigated for activity in preemergence and postemergence tests according to the following procedure:

Flats were filled with a steam-sterilized sandy loam soil. Seeds of the following test plant species were planted in furrows: cotton (*Gossypium hirsutum*) or limabean (*Phaseolus limensis*), field corn (*Zea mays L.*), soybean (*Glycine max*), wheat (*Triticum aestivum*), barnyardgrass (*Echinochloa crus galli*), johnsongrass (*Sorghum halepense*), pitted morningglory (*Ipomoea lacunosa*), velvetleaf (*Abutilon theophrasti*), field bindweed (*Convolvulus arvenia*), and green foxtail (*Setaria viridis*). Soil was leveled to a 1 cm depth over the seeds.

In both the preemergence and postemergence tests the test chemicals were applied as aqueous acetone solutions at a rate equivalent to 8.0 kilograms/hectare.

A flat for premergence test was watered and the soil evenly drenched with the water-acetone solution of test chemical. The treated flat was placed in a greenhouse where it was watered regularly at the soil surface for a period of 13 days. The effect of the test chemical was then recorded. In some tests individual plant species were examined for percent kill and a vigor rating of one to five was assigned to the surviving plants, a vigor of five signifying no chemical injury. In other tests percent kill and vigor rating were combined in a single rating called "percent control," which has the following significance:

| Percent Control | Description of Effect | Effect on Crops | Effect on Weeds |
|---|---|---|---|
| 0 | No effect | No crop reduction | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no recovery | Moderate weed control |
| 70 | | Heavy injury and stand loss | Control somewhat less than satisfactory |
| 80 | Severe effect | Crop nearly destroyed a few survivors | Satisfactory to good weed control |
| 90 | | Only occasional live plants left | Very good to excellent control |
| 100 | Completely effective | Complete crop destruction | Complete weed destruction |

Footnotes denoting other morphological responses observed were also recorded.

A flat for postemergence test was placed in a greenhouse for an 8 to 10 day growing period. The test solution was then hand-sprayed onto the foliage of the merged test plants. After spraying, the foliage of the test plants was kept dry for 24 hours after which time regular watering was resumed for a period of 13 days. The effect of the test chemical was then recorded in the same manner described for the preemergence tests.

The results of the preemergence and postemergence tests appear in Tables I and II, respectively. In the Tables, columns headed "PC," "V," "K," and "F" refer to percent control, vigor, kill, and footnotes, respectively. Footnotes B, C, D, E, G, H, J, M, P, Q, and U, defined in the Tables and described in more detail below, indicate plant growth regulator activity.

Stunting (footnote B) can retard the growth of grasses, which reduces maintenance time for lawns, golf courses, and highway rights-of-way. Stunting in fruit trees may reduce stem growth, which can reduce pruning and trimming time. Stunting in cereal and broadleaf crops such as wheat, cotton, and soybeans may result in a shorter, thicker stalk which resists lodging, in turn promoting higher yields.

Desiccation (footnote C) can reduce the pre-harvest moisture content in cereals such as wheat, or in broadleaf crops such as sunflower. Desiccation can result in the loss of foliage, and in such plants as soybeans, cotton, peanuts, and potatoes the loss of foliage aids in harvesting.

Axillary growth stimulation (footnote D), or branching, can lead to multiple stems in cereals such as wheat (tillering). An increase in the number of stems may increase the yield. In soybeans, axillary stimulation at flowering can result in more fruits, increasing yield.

Nastic response (footnote E) is manifested by twisting and bending of the plants and indicates a hormonal disruption. A natural and useful nastic response is the curling of a tendril or stem around a support, e.g., in peas and pole beans.

Stimulation (footnote G) of vegetative growth in crops such as clover results in increased yields of forage. The stimulation of reproductive growth in fruits and cereals will also result in increased yields from those crops.

Defoliation (footnote H), or loss of plant foliage just prior to harvesting crops such as soybeans, cotton, peanuts and potatoes will facilitate harvest of those crops. Foliage present at the time cotton is harvested may stain the cotton.

Intumescence (footnote J) indicates formation of abnormal swellings, a disruption of the hormonal balance that promotes normal growth. Intumescence-causing agents can promote the growth of tissue, such as tobacco callus.

Negative root geotropism (footnote M) connotes the upward growth of roots out of the soil and indicates disruption of the plant's normal hormonal balance. There can be a correlation between negative root geotropism and increase in the number of pods on soybean plants.

Deeper green lower leaves (footnote P) suggests delay of senescence, increased chlorophyll product, or chlorophyll retention. These phenomena mean greater photosynthesis, which may increase yield from plants such as soybeans.

Leaf alteration (footnote Q) indicates disruption in the plant's hormonal balance. Leaves of plants can be altered to allow better utilization of sunlight, which may enhance plant growth.

Benzoxazoles of this invention were also found in separate tests to inhibit the transport of auxin in excised stems of soybean plants, to affect geotropic response in cress (*Lepidium sativum*) seedlings, and to enhance pod set in soybean plants.

TABLE I

Preemergence Tests
Plant

| Example | Barngr | | | Bindweed | | | Corn-F | | | Greenfox | | |
|---|---|---|---|---|---|---|---|---|---|---|---|---|
| | V | PC or K | F | V | PC or K | F | V | PC or K | F | V | PC or K | F |
| 1 | 4 | 0 | BE | 3 | 60 | BE | 4 | 0 | M | 4 | 0 | B |
| 2 | 4 | 0 | I | 4 | 0 | A | 3 | 0 | ABM | 4 | 0 | B |
| 3 | 4 | 0 | AB | 4 | 20 | AB | 4 | 0 | ABM | 4 | 0 | ABM |
| 4 | 5 | 0 | 0 | 4 | 0 | A | 5 | 0 | 0 | 4 | 0 | A |
| 5 | 4 | 0 | AM | 4 | 25 | BM | 3 | 0 | BM | 3 | 0 | ABM |
| 6 | | | | | | | | | | | | |
| 7 | 3 | 0 | ABEI | 3 | 60 | ABE | 3 | 0 | ABM | 3 | 0 | AB |
| 8 | 4 | 0 | M | 3 | 30 | BEI | 3 | 0 | ABM | 4 | 0 | BIM |
| 9 | 4 | 0 | M | 3 | 0 | ABM | 4 | 0 | 0 | 4 | 0 | M |
| 10 | 5 | 0 | 0 | 4 | 0 | B | 4 | 70 | B | 4 | 50 | 0 |
| 11 | 4 | 0 | M | 4 | 0 | AI | 4 | 30 | KM | 5 | 0 | 0 |
| 12 | 5 | 0 | 0 | 5 | 0 | 0 | 4 | 30 | M | 5 | 0 | 0 |
| 13 | 4 | 0 | AB | 4 | 0 | B | 4 | 0 | ABI | 5 | 0 | 0 |
| 14 | 4 | 0 | A | 5 | 0 | 0 | 4 | 0 | M | 4 | 0 | A |
| 15 | 5 | 0 | 0 | 4 | 10 | ABI | 4 | 0 | A | 4 | 10 | A |
| 16 | 2 | 30 | ABE | 3 | 40 | ABE | 2 | 0 | ABE | 3 | 40 | ABE |
| 17 | 3 | 0 | ABE | 3 | 30 | ABE | 4 | 0 | 0 | 3 | 40 | ABE |
| 18 | 3 | 0 | ABNE | 3 | 40 | BE | 2 | 0 | ABE | 4 | 0 | BEI |
| 19 | 2 | 20 | ABE | 2 | 80 | ABE | 2 | 30 | ABE | 3 | 90 | ABE |
| 20 | 3 | 0 | BEP | 2 | 30 | ABE | 4 | 30 | ABE | 5 | 0 | 0 |
| 21 | 3 | 50 | BEP | 3 | 10 | BE | 2 | 0 | BE | 3 | 70 | B |
| 22 | 3 | 0 | ABE | 3 | 20 | ABEI | 3 | 0 | ABEI | 3 | 0 | ABE |
| 23 | 3 | 0 | E | 1 | 90 | ABE | 2 | 0 | ABE | 1 | 95 | ABE |
| 24 | 3 | 0 | ABE | 3 | 20 | ABE | 2 | 0 | ABE | 2 | 35 | ABE |
| 25 | 3 | 0 | AB4E | 3 | 50 | BE | 2 | 30 | AB2E | | | |
| 26 | 5 | 0 | 0 | 5 | 0 | 0 | 5 | 0 | 0 | 5 | 0 | 0 |
| 27 | 20 | | E | 80 | | B | 30 | | BEM | 90 | | B5 |
| 28 | 70 | | B5 | 50 | | 0 | 30 | | B2M | 90 | | B5 |
| 29 | 30 | | B1MP | 0 | | 0 | 20 | | B2EMP | 10 | | B2P |
| 30 | 10 | | M | 10 | | BIE | 20 | | MI | 20 | | B1E |
| 31 | 0 | | M | 0 | | 0 | 10 | | MP | 0 | | 0 |
| 32 | 3 | 0 | AB | 3 | 0 | ABE | 4 | 0 | M | 3 | 40 | ABE |
| 33 | 4 | 0 | M | 4 | 30 | BE | 3 | 0 | MP | 3 | 60 | ABEP |
| 34 | 5 | 0 | 0 | 3 | 30 | BE | 4 | 0 | A | 4 | 10 | AB |
| 35 | 4 | 0 | B | 4 | 40 | B | 4 | 0 | A | 4 | 20 | B |
| 36 | 5 | 0 | 0 | 4 | 0 | B | 5 | 0 | 0 | 4 | 30 | B |
| 37 | 5 | 0 | 0 | 5 | 0 | 0 | 5 | 0 | 0 | 5 | 0 | 0 |
| 38 | 5 | 0 | 0 | 5 | 0 | 0 | 5 | 0 | 0 | 5 | 0 | 0 |
| 39 | 5 | 0 | 0 | 5 | 0 | 0 | 4 | 0 | A | 5 | 0 | 0 |
| 40 | 5 | 0 | 0 | 4 | 30 | A | 4 | 0 | M | 3 | 50 | BEI |
| 41 | 4 | 0 | A | 5 | 0 | 0 | 5 | 0 | 0 | 4 | 0 | A |
| 42 | 4 | 0 | E | 4 | 0 | E | 4 | 0 | M | 3 | 0 | BI |
| 43 | 4 | 0 | A | 4 | 0 | A | 4 | 30 | 0 | 4 | 0 | A |
| 44 | 5 | 0 | 0 | 4 | 0 | B | 4 | 0 | M | 4 | 0 | AB |
| 45 | 5 | 0 | 0 | 4 | 30 | B | 4 | 30 | 0 | 4 | 0 | B |
| 46 | 5 | 0 | 0 | 5 | 0 | 0 | 5 | 0 | 0 | 5 | 0 | 0 |

| Example | Mrnglory | | | Johngr | | | Cotton[1]/ Lima Bean | | | Soybean | | | Velvetlf | | | Wheat | | |
|---|---|---|---|---|---|---|---|---|---|---|---|---|---|---|---|---|---|---|
| | V | PC or K | F | V | PC or K | F | V | PC or K | F | V | PC or K | F | V | PC or K | F | V | PC or K | F |
| 1 | — | — | — | 4 | 0 | BE | 4 | 0 | B | 4 | 0 | BE | 3 | 60 | BE | 4 | 0 | BE |
| 2 | 4 | 0 | M | 4 | 0 | AB | 4 | 0 | BM | 3 | 0 | BIM | 4 | 0 | BI | 3 | 0 | AB |
| 3 | 4 | 20 | A | 4 | 0 | M | 4 | 0 | BM | 3 | 0 | BM | 3 | 50 | AB | 4 | 0 | A |
| 4 | 4 | 0 | A | 5 | 0 | 0 | 5 | 0 | 0 | 5 | 0 | 0 | 5 | 0 | 0 | 5 | 0 | 0 |
| 5 | 4 | 0 | BM | 4 | 0 | M | 3 | 80 | BEM | 3 | 20 | BM | 4 | 0 | BM | 4 | 0 | M |
| 6 | | | | | | | | | | | | | | | | | | |
| 7 | 4 | 0 | ABE | 4 | 0 | BE | 3 | 0 | ABIM | 2 | 50 | AB | 4 | 20 | AB | 4 | 0 | AE |
| 8 | 3 | 40 | BM | 4 | 0 | M | 4 | 50 | BM | 3 | 30 | BMP | 4 | 0 | BIM | 5 | 0 | 0 |
| 9 | 4 | 0 | BM | 4 | 0 | M | 4 | 0 | I | 4 | 0 | M | 3 | 95 | BM | 4 | 0 | A |
| 10 | 4 | 0 | B | 4 | 20 | B | 4 | 80 | B | 4 | 20 | B | 4 | 0 | B | 4 | 0 | A |
| 11 | 4 | 0 | M | 4 | 0 | M | 4 | 0 | BM | 4 | 10 | AEIM | 5 | 0 | 0 | 4 | 0 | M |
| 12 | 5 | 0 | 0 | 5 | 0 | 0 | 4 | 70 | B | 4 | 50 | 0 | 5 | 0 | 0 | 5 | 0 | 0 |
| 13 | 5 | 0 | 0 | 5 | 0 | 0 | 5 | 0 | 0 | 4 | 50 | B | 5 | 0 | 0 | 4 | 0 | A |
| 14 | 4 | 0 | A | 5 | 0 | 0 | 4 | 0 | M | 4 | 0 | AM | 5 | 0 | 0 | 4 | 0 | A |
| 15 | 3 | 20 | AB | 4 | 0 | B | 5 | 0 | 0 | 4 | 20 | BI | 4 | 0 | B | 5 | 0 | 0 |
| 16 | 3 | 0 | ABE | 3 | 0 | ABE | 2 | 80 | BE | 2 | 50 | ABE | 3 | 0 | ABE | 3 | 0 | ABE |
| 17 | 3 | 30 | ABE | 3 | 0 | ABE | 3 | 30 | BE | 2 | 30 | BE | 3 | 40 | ABEI | 3 | 0 | ABE |
| 18 | 3 | 0 | ABEI | 3 | 0 | ABE | 3 | 20 | ABE | 3 | 30 | ABE | 3 | 0 | BEI | 3 | 0 | ABE |
| 19 | 2 | 10 | ABE | 3 | 10 | ABE | 3 | 50 | ABE | 3 | 70 | ABE | 3 | 80 | BE | 3 | 20 | ABE |
| 20 | 3 | 0 | ABE | 3 | 0 | M | 2 | 30 | UBE | 2 | 50 | ABE | 2 | 40 | ABE | 4 | 0 | E |
| 21 | 3 | 20 | BE | 2 | 0 | BE | 2 | 80 | ABE | 2 | 90 | BE | 3 | 10 | BE | 3 | 0 | BEP |
| 22 | 3 | 30 | BE | 3 | 0 | ABE | 3 | 70 | ABEI | 3 | 20 | ABD | 3 | 0 | EI | 3 | 30 | ABEM |
| 23 | 2 | 50 | ABE | 3 | 0 | E | 3 | 0 | ABE | 2 | 50 | ABE | 0 | 100 | 0 | 3 | 0 | AE |
| 24 | 3 | 20 | ABE | 3 | 0 | ABE | 3 | 30 | ABE | 3 | 0 | BEI | 3 | 30 | ABE | 2 | 0 | ABE |
| 25 | 3 | 20 | BE | 3 | 20 | B4E | 3 | 30 | B4EI | 2 | 20 | B4E | | | | 3 | 0 | B3E |
| 26 | 5 | 0 | 0 | 5 | 0 | 0 | 4 | 0 | B1 | 3 | 0 | B1E | 5 | 0 | 0 | 5 | 0 | 0 |
| 27 | 30 | | EB | 0 | | 0 | 30 | | A | 70 | | B5 | 0 | | E | 20 | | EB1 |
| 28 | 40 | | BE | 50 | | B3 | 50 | | B2G | 50 | | B5U | 0 | | 0 | 30 | | E |
| 29 | 40 | | B2E | 10 | | PE | 60 | | B2E | 70 | | B3E | 20 | | B1E | 50 | | B2E |
| 30 | 30 | | B2E | 10 | | M | 30 | | B2M | 70 | | B5EM | 30 | | B1EI | 60 | | B2E |
| 31 | 0 | | 0 | 40 | | B2M | 20 | | B2M[1] | 40 | | B3EM | 0 | | 0 | 20 | | B2E |
| 32 | 3 | 0 | ABE | 4 | 0 | ABE | 2 | 50 | BEM | 3 | 0 | BDI | 3 | 0 | BE | 3 | 0 | ABM |
| 33 | 4 | 50 | BEM | 4 | 0 | M | 4 | 0 | M | 3 | 50 | BEM | 5 | 0 | 0 | 3 | 0 | EM |
| 34 | 4 | 0 | BEI | 5 | 0 | 0 | 3 | 80 | B | 4 | 60 | B | 3 | 90 | BI | 4 | 0 | A |
| 35 | 4 | 0 | B | 5 | 0 | 0 | 5 | 0 | 0 | 4 | 0 | B | 4 | 50 | 0 | 4 | 0 | A |
| 36 | 5 | 0 | 0 | 5 | 0 | 0 | 4 | 0 | BM | 4 | 0 | B | 4 | 30 | B | 5 | 0 | 0 |
| 37 | 5 | 0 | 0 | 5 | 0 | 0 | 5 | 0 | 0 | 5 | 0 | 0 | 5 | 0 | 0 | 5 | 0 | 0 |
| 38 | 5 | 0 | 0 | 5 | 0 | 0 | 5 | 0 | 0 | 5 | 0 | 0 | 5 | 0 | 0 | 5 | 0 | 0 |
| 39 | 5 | 0 | 0 | 5 | 0 | 0 | 4 | 0 | AI | 5 | 0 | 0 | 5 | 0 | 0 | 5 | 0 | 0 |
| 40 | 4 | 0 | M | 4 | 0 | M | 4 | 0 | M | 4 | 0 | M | 4 | 20 | BM | 4 | 0 | M |
| 41 | 4 | 0 | A | 5 | 0 | 0 | 4 | 0 | AM | 4 | 0 | BM | 5 | 0 | 0 | 5 | 0 | 0 |
| 42 | 4 | 0 | B | 4 | 0 | BI | 4 | 0 | B | 3 | 0 | ABDI | 4 | 0 | A | 5 | 0 | 0 |
| 43 | 4 | 0 | E | 5 | 0 | 0 | 5 | 0 | 0 | 5 | 0 | 0 | 4 | 0 | A | 5 | 0 | 0 |
| 44 | 4 | 0 | BM | 4 | 0 | 0 | 4 | 0 | IM | 4 | 0 | M | 0 | 100 | 0 | 4 | 0 | M |
| 45 | 4 | 50 | 0 | 5 | 0 | 0 | 5 | 0 | 0 | 5 | 0 | 0 | 5 | 0 | 0 | 5 | 0 | 0 |
| 46 | 5 | 0 | 0 | 5 | 0 | 0 | 5 | 0 | 0 | 4 | 0 | B | 5 | 0 | 0 | 5 | 0 | 0 |

TABLE I-continued

Preemergence Tests — Plant

| Example | Barngr V | Barngr PC or K | Barngr F | Bindweed V | Bindweed PC or K | Bindweed F | Corn-F V | Corn-F PC or K | Corn-F F | Greenfox V | Greenfox PC or K | Greenfox F | Mrnglory V | Mrnglory PC or K | Mrnglory F | Johngr V | Johngr PC or K | Johngr F | Cotton[1]/Lima Bean V | Cotton[1]/Lima Bean PC or K | Cotton[1]/Lima Bean F | Soybean V | Soybean PC or K | Soybean F | Velvetlf V | Velvetlf PC or K | Velvetlf F | Wheat V | Wheat PC or K | Wheat F |
|---|---|---|---|---|---|---|---|---|---|---|---|---|---|---|---|---|---|---|---|---|---|---|---|---|---|---|---|---|---|---|
| 47 | 5 | 0 | 0 | 5 | 0 | 0 | 4 | 0 | M | 4 | 0 | A | 5 | 0 | 0 | 5 | 0 | 0 | 4 | 50 | BM | 5 | 0 | 0 | 5 | 0 | 0 | 5 | 0 | 0 |
| 48 | 5 | 0 | 0 | 5 | 0 | 0 | 5 | 0 | 0 | 4 | 0 | AI | 4 | 0 | I | 4 | 0 | N | 5 | 0 | 0 | 5 | 0 | 0 | 5 | 0 | 0 | 5 | 0 | 0 |
| 49 | 4 | 0 | A | 5 | 0 | 0 | 4 | 0 | M | 4 | 0 | A | 4 | 0 | A | 4 | 0 | A | 4 | 0 | AM | 4 | 70 | ABEM | 5 | 0 | 0 | 4 | 0 | AM |
| 50 | 5 | 0 | 0 | 5 | 0 | 0 | 4 | 0 | BM | 5 | 0 | 0 | 5 | 0 | 0 | 5 | 0 | 0 | 4 | 10 | M | 4 | 0 | B | 5 | 0 | 0 | 4 | 0 | B |
| 51 | 3 | 0 | ABE | 3 | 50 | ABEP | 4 | 0 | M | 2 | 80 | AB | 3 | 10 | BE | 4 | 0 | ABEP | 4 | 0 | M | 3 | 40 | ABDP | 4 | 0 | B | 3 | 20 | ABE |
| 52 | 4 | 0 | ABE | 4 | 0 | ABE | 4 | 0 | BI | 5 | 0 | 0 | 3 | 0 | BE | 4 | 0 | ABE | 3 | 0 | BE | 3 | 0 | BDEI | 4 | 0 | A | 4 | 0 | A |
| 53 | 3 | 0 | BEM | 3 | 30 | BEI | 4 | 30 | AIM | 3 | 0 | BE | 4 | 20 | BM | 4 | 0 | M | 4 | 0 | M | 3 | 40 | BIM | | | | 3 | 10 | BEI |
| 54 | 3 | 0 | ABE | 3 | 50 | BE | 2 | 30 | ABE | 0 | 100 | 0 | 3 | 0 | BE | 3 | 0 | BE | 3 | 50 | ABE | 3 | 50 | BDE | 3 | 0 | BE | 3 | 0 | BE |
| 55 | 3 | 0 | BEP | 4 | 0 | E | 4 | 0 | BM | 3 | 0 | BEP | 3 | 0 | BE | 3 | 0 | BE | 3 | 0 | B | 3 | 50 | BEM | 4 | 0 | E | 3 | 0 | BEP |
| 56 | 4 | 0 | M | 5 | 0 | 0 | 4 | 0 | M | 3 | 0 | BEM | 4 | 0 | A | 3 | 0 | EM | 3 | 0 | AEI | 3 | 20 | BEM | 5 | 0 | 0 | 4 | 0 | M |
| 57 | 3 | 0 | AEI | 3 | 0 | EI | 4 | 0 | IM | 3 | 0 | BE | 4 | 0 | M | 3 | 0 | BE | 3 | 20 | EM | 3 | 30 | BDI | 3 | 0 | EI | 3 | 0 | AEIM |
| 58 | 3 | 0 | BEP | 4 | 0 | 3 | 4 | 0 | M | 3 | 0 | BEP | 3 | 0 | BE | 3 | 0 | BE | 3 | 0 | ABE | 3 | 0 | ABE | 3 | 20 | BE | 3 | 0 | BEP |
| 59 | 3 | 0 | BM | 3 | 0 | B | 4 | 0 | M | 4 | 0 | A | 4 | 0 | 3 | 3 | 0 | BE | 5 | 0 | 0 | 3 | 0 | E | 4 | 0 | E | 4 | 0 | BE |
| 60 | 3 | 10 | AB4E | 3 | 90 | BE | 2 | 30 | AB3E | 3 | 0 | AB4E | 3 | 30 | BE | 3 | 50 | B4E | 3 | 0 | B3 | 3 | 0 | AB4E | 3 | 0 | BE | 3 | 0 | E |
| 61 | 10 | | AB1 | 20 | | AB1 | 0 | | 0 | 40 | | AB2E | 0 | | 0 | 10 | | AB2 | 0 | | 0 | 0 | | 0 | 0 | | 0 | 0 | | 0 |
| 62 | 5 | 0 | 0 | 5 | 0 | 0 | 4 | 0 | M | 5 | 0 | 0 | 4 | 0 | M | 5 | 0 | 0 | 5 | 0 | 0 | 5 | 0 | 0 | 5 | 0 | 0 | 5 | 0 | 0 |
| 63 | 60 | | B3EAPB5 | 100 | | 0 | 100 | | 0 | 100 | | 0 | 90 | | BE4 | 90 | | B4EA | 90 | | B5E | 100 | | 0 | 100 | | 0 | 100 | | 0 |
| 64 | 0 | | 0 | 0 | | 0 | 0 | | 0 | 0 | | 0 | 0 | | 0 | 0 | | 0 | 0 | | 0 | 0 | | 0 | 0 | | 0 | 0 | | 0 |
| 65 | 0 | | 0 | 20 | | BEI | 20 | | B2E | 0 | | 0 | 0 | | 0 | 0 | | 0 | 0 | | 0 | 10 | | B1 | 0 | | 0 | 40 | | B2E |
| 66 | 0 | | 0 | 0 | | 0 | 0 | | M | 0 | | 0 | 0 | | 0 | 0 | | 0 | 0 | | 0 | 0 | | 0 | 0 | | 0 | 10 | | B1M |
| 67 | 0 | | 0 | 0 | | 0 | 30 | | B1A | 0 | | 0 | 0 | | 0 | 0 | | 0 | 30 | | B2 | 20 | | B1 | 0 | | 0 | 60 | | B2E |
| 68 | 4 | 0 | M | 4 | 0 | AE | 4 | 0 | AM | 4 | 0 | BM | 5 | 0 | 0 | 4 | 0 | M | 4 | 0 | BEM | 4 | 0 | BM | 4 | 0 | A | 4 | 0 | AM |
| 69 | 5 | 0 | 0 | 5 | 0 | 0 | 4 | 0 | B | 5 | 0 | 0 | 4 | 0 | B | 5 | 0 | 0 | 5 | 0 | 0 | 4 | 50 | BEM | 5 | 0 | 0 | 5 | 0 | 0 |
| 70 | 5 | 0 | 0 | 4 | 50 | A | 4 | 0 | A | 4 | 10 | A | 5 | 0 | 0 | 5 | 0 | 0 | 5 | 0 | 0 | 5 | 0 | 0 | 5 | 0 | 0 | 5 | 0 | 0 |
| 71 | 5 | 0 | 0 | 5 | 0 | 0 | 4 | 0 | M | 5 | 0 | 0 | 5 | 0 | 0 | 5 | 0 | 0 | 4 | 0 | M | 4 | 0 | M | 5 | 0 | 0 | 5 | 0 | 0 |
| 72 | 4 | 0 | B | 3 | 90 | B | 4 | 0 | BM | 4 | 0 | B | 4 | 0 | B | 4 | 0 | B | 4 | 0 | B | 3 | 40 | B | 4 | 60 | B | 4 | 20 | BE |
| 73 | 5 | 0 | 0 | 4 | 40 | 0 | 4 | 0 | M | 4 | 30 | 0 | 0 | 100 | 0 | 4 | 0 | B | 4 | 0 | M | 5 | 0 | 0 | 4 | 30 | 0 | 5 | 0 | 0 |
| 74 | 4 | 0 | M | 4 | 0 | A | 4 | 0 | AM | 4 | 0 | AM | 4 | 0 | M | 4 | 0 | M | 4 | 0 | AB | 3 | 0 | B | 4 | 20 | A | 4 | 0 | AM |
| 75 | 5 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | 0 |
| 76 | 4 | 0 | M | 4 | 0 | BM | 4 | 0 | M | 4 | 0 | BM | 4 | 0 | BM | 4 | 0 | M | 4 | 20 | M | 4 | 0 | BM | 4 | 0 | M | 4 | 0 | M |
| 77 | 4 | 0 | M | 4 | 0 | BEM | 3 | 0 | BM | 4 | 0 | M | 3 | 0 | BEM | 4 | 0 | M | 4 | 0 | BM | 4 | 30 | EM | 4 | 0 | M | 4 | 0 | M |
| 78 | 3 | 0 | AB | 4 | 0 | A | 3 | 0 | M | 4 | 0 | BM | 4 | 0 | M | 4 | 0 | B | 4 | 0 | AM | 3 | 40 | BM | 4 | 20 | A | 4 | 0 | AM |
| 79 | 4 | 0 | BM | 3 | 30 | EI | 3 | 0 | ABMP | 4 | 0 | M | 3 | 40 | BEM | 4 | 0 | M | 3 | 10 | BM | 3 | 20 | BMP | 4 | 0 | IM | 4 | 0 | AB |
| 80 | 5 | 0 | 0 | 4 | 10 | 0 | 4 | 30 | 0 | 4 | 40 | A | 3 | 80 | AB | 4 | 0 | B | 5 | 0 | 0 | 4 | 20 | B | 5 | 0 | 0 | 4 | 0 | A |
| 81 | 5 | 0 | 0 | 5 | 0 | 0 | 5 | 0 | 0 | 4 | 0 | A | 5 | 0 | 0 | 5 | 0 | 0 | 5 | 0 | 0 | 5 | 0 | 0 | 5 | 0 | 0 | 5 | 0 | 0 |
| 82 | 4 | 0 | BEM | 3 | 95 | B | 4 | 0 | ABM | 2 | 95 | B | 3 | 20 | BE | 4 | 0 | M | 4 | 0 | AIM | 3 | 60 | BIM | 3 | 20 | BI | 4 | 0 | AE |
| 83 | 2 | 30 | ABE | 4 | 0 | AE | 2 | 0 | ABE | 3 | 30 | ABE | 3 | 30 | ABE | 3 | 0 | ABE | 0 | 100 | 0 | 2 | 70 | ABE | 4 | 40 | AB | 3 | 0 | ABE |
| 84 | 3 | 0 | ABEP | 3 | 40 | ABE | 4 | 0 | ABMP | 3 | 40 | ABEP | 3 | 20 | ABE | 4 | 0 | ABEP | 2 | 30 | ABMP | 3 | 20 | ABMP | 3 | 50 | ABE | 3 | 0 | ABEP |
| 85 | 3 | 10 | BE | 3 | 40 | ABE | 2 | 0 | ABE | 3 | 40 | ABE | 2 | 30 | ABE | 3 | 10 | BE | 3 | 20 | ABE | 2 | 70 | ABE | 3 | 50 | B | 3 | 0 | BE |
| 86 | 3 | 0 | BE | 3 | 90 | BE | 2 | 30 | ABEM | 2 | 80 | BE | 3 | 20 | BE | 2 | 0 | BEP | 3 | 10 | ABEM | 2 | 80 | BE | 2 | 90 | BE | 4 | 0 | E |
| 87 | 3 | 0 | BE | 3 | 10 | BE | 4 | 30 | EM | 5 | 0 | 0 | 3 | 0 | BE | 3 | 0 | BE | 3 | 0 | ABEI | 3 | 40 | BD | 4 | 0 | EI | 4 | 0 | BEM |
| 88 | 3 | 0 | BE | 2 | 40 | BE | 2 | 30 | ABEK | 2 | 0 | BE | 2 | 0 | BE | 3 | 0 | BE | 2 | 30 | ABE | 1 | 90 | ABE | 1 | 95 | BE | 2 | 0 | BE |
| 89 | 3 | 0 | ABE | 3 | 10 | ABE | 2 | 0 | ABE | 3 | 0 | BE | 0 | 100 | 0 | 3 | 0 | ABE | 3 | 20 | ABE | 3 | 20 | BE | 3 | 0 | BE | 3 | 0 | ABE |
| 90 | 3 | 0 | AB4E | 3 | 30 | BE | 2 | 0 | AB3E | 3 | 0 | B4E | 3 | 30 | BE | 3 | 10 | AB4E | 3 | 90 | B4E | 3 | 90 | BE | | | | 3 | 0 | AB3E |
| 91 | 4 | 0 | B1 | 5 | 0 | 0 | 4 | 0 | B1M | 5 | 0 | 0 | 5 | 0 | 0 | 4 | 0 | B1 | 4 | 0 | B1E | 4 | 0 | B1M | 5 | 0 | 0 | 4 | 0 | B1E |
| 92 | 50 | | B5E | 50 | | E | 0 | | GMP | 90 | | B56 | 40 | | BE | 40 | | B5E | 30 | | E | 50 | | B3E | 0 | | E | 30 | | E |

TABLE I-continued

Preemergence Tests — Plant

| Ex-ample | Barngr V | Barngr PC or K | Barngr F | Bindweed V | Bindweed PC or K | Bindweed F | Corn-F V | Corn-F PC or K | Corn-F F | Greenfox V | Greenfox PC or K | Greenfox F | Mrnglory V | Mrnglory PC or K | Mrnglory F | Johngr V | Johngr PC or K | Johngr F | Cotton[1]/ Lima Bean V | Cotton[1]/ Lima Bean PC or K | Cotton[1]/ Lima Bean F | Soybean V | Soybean PC or K | Soybean F | Velvetlf V | Velvetlf PC or K | Velvetlf F | Wheat V | Wheat PC or K | Wheat F |
|---|---|---|---|---|---|---|---|---|---|---|---|---|---|---|---|---|---|---|---|---|---|---|---|---|---|---|---|---|---|---|
| 93 | 80 | | B5 | 70 | | 0 | 50 | | B3M | 60 | | B3 | 0 | | E | 50 | | B3E | 50 | | B3 | 80 | | B5 | 50 | | 0 | 40 | | B1E |
| 94 | 30 | | B2MP | 0 | | 0 | 20 | | MI | 90 | | B5 | 90 | | B4AE | 10 | | MP | 80 | | B3EA | 90 | | B5E | 0 | | 0 | 40 | | B2E |
| 95 | 4 | 0 | ABM | 3 | 50 | ABE | 4 | 0 | AM | 3 | 40 | AB | 3 | 40 | B | 4 | 0 | AM | 3 | 90 | B | 3 | 50 | BE | 3 | 90 | ABI | 4 | 0 | A |
| 96 | 5 | 0 | 0 | 5 | 0 | 0 | 4 | 0 | AM | 5 | 0 | 0 | 5 | 0 | 0 | 5 | 0 | 0 | 5 | 0 | 0 | 4 | 20 | B | 5 | 0 | 0 | 5 | 0 | 0 |
| 97 | 30 | | 0 | 90 | | B | 40 | | B2MP | 90 | | 0 | 80 | | AB | 50 | | AB2 | 70 | | 0 | 100 | | 0 | 90 | | BEI | 40 | | 0 |
| 98 | 60 | | B5 | 40 | | BE | 40 | | B3EM | 40 | | B5E | 30 | | BE | 40 | | B5E | 40 | | B5E | 60 | | B5 | 20 | | BE | 40 | | B2E |
| 99 | 10 | | AB2 | 20 | | AB1E | 20 | | B1M | 10 | | AB1 | 0 | | B1E | 0 | | 0 | 30 | | AB1 | 10 | | B2 | 0 | | 0 | 30 | | B1E |
| 100 | 80 | | B5E | 60 | | BE | 70 | | AB3EM | 80 | | B5E | 60 | | BE | 80 | | B5E | 60 | | B5E[1] | 90 | | B4E | 60 | | BEI | 60 | | AB2EI |
| 101 | 80 | | B5EP | 10 | | B1E | 30 | | B2EP | 90 | | B5EA | 80 | | B5E | 80 | | B5E | 80 | | B5E[1] | 90 | | B5E | 40 | | B2E | 50 | | B2EA |
| 102 | 0 | | 0 | 10 | | AB2 | 70 | | B1K | 10 | | B1 | 10 | | B3 | 10 | | B2M | 20 | | AB2[1] | 60 | | B2 | 10 | | B3 | 30 | | B2 |
| 103 | 20 | | AB4 | 0 | | 0 | 10 | | AB1 | 0 | | 0 | 10 | | B | 20 | | AB1 | 0 | | 0[1] | 0 | | 0 | 10 | | 0 | 0 | | 0 |
| 104 | 30 | | E | 0 | | 0 | 10 | | B2M | 0 | | 0 | 0 | | 0 | 0 | | 0 | 20 | | B2E[1] | 10 | | B2M | 0 | | 0 | 10 | | B1E |
| 105 | 60 | | B5P | 10 | | E | 30 | | EPMB2 | 30 | | B5 | 40 | | BE | 50 | | 0 | 0 | | 0[1] | 0 | | 0 | 60 | | B | 10 | | E |
| 106 | 80 | | B5 | 50 | | BE | 30 | | PM | 40 | | B3 | 70 | | BE | 50 | | B3 | 10 | | B1[1] | 20 | | B3 | 70 | | BE | 10 | | E |
| 107 | 0 | | 0 | 0 | | 0 | 10 | | M | 80 | | B3AE | 20 | | B1EM | 20 | | B1AM | 10 | | B1M[1] | 60 | | B3M | 0 | | 0 | 30 | | B2M |
| 108 | 20 | | B1E | 0 | | 0 | 30 | | B2EM | 80 | | B5E | 30 | | B1E1 | 20 | | PEM | 90 | | B3EMA[1] | 60 | | B3PEM | 10 | | L | 20 | | EM |

FOOTNOTES
V = Vigor
5 = Plants normal
4 = Slight injury; plants will or have already recovered
3 = Moderate injury; plants expected to recover
2 = Moderate to severe injury; plants are not expected to recover
1 = Severe injury; plants will not recover
0 = Dead plant
K = % Kill
F = Footnote:
A = Necrosis
B = Stunted
C = Desiccation
D = Axillary Growth Stimulation
E = Nastic Responses
F = Necrotic Spots
G = Growth Stimulation
H = Defoliant
I = Chlorosis
J = Intumescence
K = Suspected germination failure
L = Stand may be affected by non-chemical factors
M = Negative root geotropism
N = Bleaching
P = Deeper green lower leaves
Q = Leaf alterations
U = Any other morphological response
Sub-footnotes:
1 = 0%-24%
2 = 25%-49%
3 = 50%-74%
4 = 75%-100%
5 = refers to stunting only 75%-100% stunted with 0-30% phytotoxicity
[1]Data for cotton

TABLE II

Postemergence Tests Plant

| Example | Barngr PC or V | Barngr K | Barngr F | Bindweed PC or V | Bindweed K | Bindweed F | Corn-F PC or V | Corn-F K | Corn-F F | Greenfox PC or V | Greenfox K | Greenfox F | Mrnglory PC or V | Mrnglory K | Mrnglory F |
|---|---|---|---|---|---|---|---|---|---|---|---|---|---|---|---|
| 1 | 4 | 0 | 0 | 4 | 0 | B | 5 | 0 | 0 | 4 | 0 | A | 4 | 0 | AB |
| 2 | 4 | 0 | C | 4 | 0 | AB | 4 | 0 | M | 4 | 0 | A | 4 | 0 | AB |
| 3 | 4 | 0 | C | 4 | 0 | C | 4 | 0 | C | 4 | 0 | C | 4 | 0 | C |
| 4 | 4 | 0 | A | 3 | 80 | A | 4 | 0 | A | 4 | 0 | A | 5 | 0 | 0 |
| 5 | 5 | 0 | 0 | 5 | 0 | 0 | 5 | 0 | 0 | 5 | 0 | 0 | 5 | 0 | 0 |
| 6 | | | | | | | | | | | | | | | |
| 7 | 4 | 0 | CM | 3 | 0 | C | 4 | 0 | M | 4 | 0 | BC | 4 | 0 | CM |
| 8 | 4 | 0 | AM | 3 | 0 | E | 4 | 0 | M | 4 | 0 | 3 | 3 | 0 | BE |
| 9 | 4 | 0 | C | 4 | 90 | CI | 4 | 0 | CM | 5 | 0 | 0 | 4 | 0 | CI |
| 10 | 5 | 0 | 0 | 3 | 95 | AB | 5 | 0 | 0 | 5 | 0 | 0 | 4 | 0 | A |
| 11 | 4 | 0 | C | 0 | 100 | 0 | 4 | 0 | CM | 4 | 0 | CIM | 4 | 0 | CM |
| 12 | 4 | 0 | C | 3 | 30 | BCM | 5 | 0 | 0 | 4 | 0 | C | 4 | 0 | C |
| 13 | 4 | 0 | A | 4 | 0 | A | 4 | 0 | A | 4 | 0 | AB | 5 | 0 | 0 |
| 14 | 4 | 0 | C | 3 | 0 | CI | 4 | 0 | C | 4 | 0 | C | 4 | 0 | C |
| 15 | 3 | 0 | A | 3 | 0 | AE | 4 | 0 | AM | 5 | 0 | 0 | 4 | 0 | AE |
| 16 | 3 | 0 | A | 3 | 20 | ABE | 3 | 0 | AM | 4 | 0 | A | 3 | 0 | BE |
| 17 | 3 | 0 | A | 2 | 0 | ABE | 4 | 0 | AM | 4 | 0 | A | 3 | 0 | AE |
| 18 | 4 | 10 | C | 3 | 30 | BDE | 3 | 0 | BCM | 5 | 0 | 0 | 3 | 40 | BCEH |
| 19 | 3 | 0 | BCE | 3 | 95 | BC | 2 | 0 | BCEM | 3 | 0 | BCE | 3 | 0 | BCEI |
| 20 | 3 | 0 | BCE | 3 | 60 | BCE | 3 | 0 | CEM | 4 | 20 | C | 2 | 50 | BCE |
| 21 | 3 | 0 | BCE | 2 | 80 | BCE | 3 | 0 | BCEM | 4 | 0 | CE | 2 | 60 | BCE |
| 22 | 4 | 0 | AB | 3 | 0 | E | 4 | 0 | M | 4 | 0 | M | 3 | 0 | ABE |
| 23 | 3 | 0 | BCE | 0 | 100 | 0 | 3 | 0 | CEM | 3 | 10 | BCE | 3 | 95 | BCE |
| 24 | 4 | 0 | C | 3 | 0 | CE | 2 | 0 | BCEM | 3 | 0 | CL | 2 | 0 | BCE |
| 25 | 4 | 0 | M | 4 | 0 | B1E | 4 | 0 | MEP | 4 | 0 | M | 4 | 0 | B1E |
| 26 | 5 | 0 | 0 | 5 | 0 | 0 | 3 | 0 | M | 5 | 0 | 0 | 5 | 0 | 0 |
| 27 | 40 | | AE | 80 | | BE | 40 | | B3 | 0 | | 0 | 60 | | EIB |
| 28 | 20 | | AM | 20 | | AB4E | 20 | | AB2M | 10 | | A | 70 | | AB2E |
| 29 | 20 | | A | 40 | | E | 0 | | M | 0 | | 0 | 30 | | ABE |
| 30 | 40 | | AB4 | 20 | | ABE | 30 | | AEM | 60 | | A | 40 | | ADE |
| 31 | 0 | | 0 | 0 | | 0 | 0 | | M | 0 | | 0 | 0 | | 0 |
| 32 | 4 | 0 | AM | 3 | 30 | BE | 4 | 0 | AM | 3 | 0 | ABM | 4 | 0 | AE |
| 33 | 3 | 0 | BC | 3 | 50 | CE | 4 | 0 | BM | 4 | 0 | CE | 3 | 0 | BCEM |
| 34 | 4 | 0 | A | 3 | 50 | ABM | 5 | 0 | 0 | 5 | 0 | 0 | 4 | 0 | A |
| 35 | 4 | 0 | A | 3 | 30 | AI | 4 | 0 | A | 4 | 30 | A | 4 | 0 | A |
| 36 | 4 | 0 | A | 5 | 0 | 0 | 4 | 0 | A | 5 | 0 | 0 | 5 | 0 | 0 |
| 37 | 5 | 0 | 0 | 2 | 30 | AB | 4 | 0 | AB | 4 | 0 | A | 5 | 0 | 0 |
| 38 | 4 | 0 | C | 4 | 0 | C | 4 | 0 | C | 4 | 0 | C | 4 | 0 | C |
| 39 | 4 | 0 | A | 4 | 0 | A | 4 | 0 | A | 4 | 0 | AB | 4 | 0 | AI |
| 40 | 4 | 0 | A | 4 | 50 | A | 4 | 0 | A | 4 | 0 | A | 5 | 0 | 0 |
| 41 | 4 | 0 | A | 4 | 0 | B | 4 | 0 | A | 4 | 0 | A | 4 | 0 | BM |
| 42 | 5 | 0 | 0 | 4 | 0 | EI | 4 | 0 | C | 3 | 40 | BC | 4 | 0 | EM |
| 43 | 4 | 0 | A | 0 | 100 | 0 | 4 | 0 | A | 4 | 0 | A | 4 | 0 | ADI |
| 44 | 4 | 0 | A | 4 | 0 | AI | 4 | 0 | A | 4 | 0 | A | 5 | 0 | 0 |
| 45 | 5 | 0 | 0 | 4 | 0 | A | 5 | 0 | 0 | 5 | 0 | 0 | 5 | 0 | 0 |
| 46 | 4 | 0 | A | 4 | 0 | AI | 4 | 0 | B | 4 | 0 | A | 4 | 0 | A |
| 47 | 4 | 0 | C | 4 | 0 | C | 5 | 0 | 0 | 4 | 0 | C | 4 | 0 | C |
| 48 | 4 | 0 | A | 3 | 20 | A | 4 | 0 | A | 4 | 0 | A | 4 | 0 | AI |
| 49 | 4 | 0 | C | 3 | 40 | C | 4 | 0 | CM | 3 | 80 | BC | 3 | 0 | BDIM |
| 50 | 4 | 0 | A | 5 | 0 | 0 | 5 | 0 | 0 | 5 | 0 | 0 | 5 | 0 | 0 |
| 51 | 4 | 0 | A | 4 | 0 | ABE | 4 | 0 | A | 4 | 0 | A | 3 | 0 | ABE |
| 52 | 4 | 0 | AM | 3 | 50 | BE | 4 | 0 | A | 0 | 100 | 0 | 3 | 0 | EM |
| 53 | 5 | 0 | 0 | 5 | 0 | 0 | 5 | 0 | 0 | 5 | 0 | 0 | 4 | 0 | AB |
| 54 | 3 | 0 | ABEM | 2 | 0 | BE | 2 | 0 | ABEM | 3 | 0 | BE | 2 | 0 | BEM |
| 55 | 3 | 0 | AB | 3 | 0 | E | 4 | 0 | BM | 3 | 0 | ABI | 3 | 0 | AEI |
| 56 | 4 | 0 | BC | 3 | 0 | BE | 4 | 0 | CM | 4 | 0 | BC | 3 | 25 | BCE |
| 57 | 4 | 0 | A | 3 | 0 | E | 4 | 0 | AM | 3 | 0 | ABE | 3 | 0 | BE |
| 58 | 3 | 0 | BCM | 2 | 90 | BCI | 2 | 30 | BCE | 3 | 0 | BC | 3 | 30 | BCEI |
| 59 | 4 | 0 | A | 3 | 30 | AE | 3 | 0 | ABEM | 3 | 40 | AB | 3 | 0 | AB |
| 60 | 4 | 0 | PM | 4 | 0 | B1E | 4 | 0 | PEM | 5 | 0 | 0 | 4 | 0 | B1E |
| 61 | 0 | | 0 | 10 | | E | 0 | | M | 30 | | B3EAP | 10 | | EB1 |
| 62 | 5 | 0 | 0 | 5 | 0 | 0 | 5 | 0 | 0 | 5 | 0 | 0 | 5 | 0 | 0 |
| 63 | 40 | | AE | 80 | | BE | 40 | | B3 | 0 | | 0 | 60 | | EIB |
| 64 | 30 | | AB1 | 20 | | A | 20 | | AB1 | 10 | | A | 30 | | AB1E |
| 65 | 20 | | A | 40 | | E | 20 | | AB1M | 0 | | 0 | 30 | | ABE |
| 66 | 0 | | 0 | 60 | | B | 10 | | M | 60 | | B2 | 90 | | BE |
| 67 | 0 | | 0 | 0 | | 0 | 0 | | 0 | 0 | | 0 | 0 | | 0 |
| 68 | 4 | 0 | A | 3 | 0 | ABE | 4 | 0 | AM | 4 | 0 | A | 4 | 0 | BE |
| 69 | 4 | 0 | A | 4 | 0 | AI | 4 | 0 | A | 4 | 0 | A | 4 | 0 | B |
| 70 | 4 | 0 | A | 4 | 0 | A | 4 | 0 | A | 4 | 0 | A | 5 | 0 | 0 |
| 71 | 5 | 0 | 0 | 4 | 0 | CI | 4 | 0 | C | 3 | 20 | BC | 5 | 0 | 0 |
| 72 | 5 | 0 | 0 | 4 | 0 | 0 | 5 | 0 | 0 | 5 | 0 | 0 | 5 | 0 | 0 |
| 73 | 4 | 0 | C | 1 | 90 | B | 4 | 0 | B | 4 | 0 | C | 5 | 0 | 0 |
| 74 | 4 | 0 | C | 3 | 40 | C | 4 | 0 | C | 3 | 30 | BC | 4 | 0 | C |
| 75 | 4 | 0 | A | 4 | 0 | A | 4 | 0 | A | 4 | 0 | A | 4 | 0 | A |
| 76 | 4 | 0 | M | 4 | 0 | M | 5 | 0 | 0 | 4 | 0 | M | 4 | 0 | M |
| 77 | 4 | 0 | BC | 3 | 20 | C | 4 | 0 | M | 5 | 0 | 0 | 4 | 0 | BC |

TABLE II-continued

Postemergence Tests Plant

| | | | | | | | | | | | | | | | |
|---|---|---|---|---|---|---|---|---|---|---|---|---|---|---|---|
| 78 | 4 | 0 | C | 3 | 0 | CE | 4 | 0 | CM | 3 | 0 | BC | 4 | 0 | CM |
| 79 | 3 | 0 | ABE | 3 | 0 | E | 3 | 0 | ABE | 3 | 0 | ABN | 3 | 0 | ABE |
| 80 | 5 | 0 | 0 | 0 | 100 | 0 | 5 | 0 | 0 | 3 | 30 | C | 4 | 0 | C |
| 81 | 5 | 0 | 0 | 3 | 40 | A | 4 | 0 | A | 4 | 20 | A | 5 | 0 | 0 |
| 82 | 4 | 0 | A | 4 | 0 | AB | 4 | 0 | A | 4 | 0 | A | 4 | 0 | ABE |
| 83 | 3 | 0 | AB | 2 | 90 | ABE | 3 | 0 | AM | 4 | 0 | AB | 3 | 0 | ABE |
| 84 | 4 | 0 | A | 4 | 0 | E | 4 | 0 | A | 4 | 0 | A | 3 | 0 | AE |
| 85 | 3 | 0 | BCE | 2 | 30 | BCE | 2 | 0 | BCEM | 3 | 0 | BCE | 3 | 0 | BCEI |
| 86 | 3 | 0 | BC | 0 | 100 | 0 | 3 | 0 | BCM | 4 | 0 | M | 2 | 80 | BCE |
| 87 | 4 | 0 | C | 3 | 0 | BCE | 3 | 0 | BCEM | 3 | 0 | BE | 3 | 40 | BCEHPM |
| 88 | 3 | 0 | BC | 0 | 100 | 0 | 3 | 0 | BCEM | 3 | 0 | BC | 0 | 100 | 0 |
| 89 | 4 | 0 | BC | 3 | 50 | BCE | 3 | 0 | BCEM | 3 | 20 | BCL | 2 | 0 | BCE |
| 90 | 5 | 0 | 0 | 3 | 0 | EB1 | 3 | 0 | ME | 3 | 0 | M | 3 | 0 | B1E |
| 91 | 3 | 0 | MI | 5 | 0 | 0 | 4 | 0 | M | | | | 3 | 0 | EM |
| 92 | 30 | | B1C2M | 20 | | B2C1E | 20 | | B1C1 | 20 | | B2C1U | 80 | | B3C3E |
| 93 | 20 | | AM | 10 | | B | 20 | | AB1M | 20 | | A | 80 | | AB3E |
| 94 | 0 | | 0 | 30 | | E | 0 | | M | 0 | | 0 | 30 | | ABE |
| 95 | 4 | 0 | A | 3 | 20 | A | 4 | 0 | AM | 4 | 0 | A | 3 | 0 | ABM |
| 96 | 5 | 0 | 0 | 5 | 0 | 0 | 4 | 0 | A | 3 | 0 | AB | 5 | 0 | 0 |
| 97 | 0 | | 0 | 0 | | 0 | 0 | | M | ND | | ND | 20 | | AEB1 |
| 98 | 20 | | AB1U | 10 | | AB2E | 40 | | AB2EM | 30 | | AB2U | 10 | | AB4PEM |
| 99 | 0 | | 0 | 10 | | 3 | 10 | | MI | 10 | | ME | 30 | | B1EM |
| 100 | 20 | | AB1 | 0 | | 0 | 30 | | E | 20 | | AB1 | 0 | | AB1E |
| 101 | 0 | | 0 | 30 | | E | 30 | | AM | 50 | | AB2E | 30 | | E |
| 102 | 0 | | 0 | 0 | | 0 | 0 | | 0 | 0 | | 0 | 0 | | 0 |
| 103 | 0 | | 0 | 0 | | 0 | 0 | | 0 | 0 | | 0 | 0 | | 0 |
| 104 | 30 | | AB1 | 20 | | E | 20 | | AB1M | 10 | | A | 20 | | AB1E |
| 105 | 70 | | L | 70 | | BE | 30 | | B2M | 40 | | B1 | 40 | | BE |
| 106 | 20 | | B5 | 40 | | BE | 30 | | B5M | 20 | | B2E | 30 | | BE |
| 107 | 20 | | A | 30 | | EI | 40 | | AB1IM | 10 | | E | 30 | | BE |
| 108 | 40 | | L | 40 | | E | 30 | | AEM | 20 | | E | 30 | | BE |

| | Johngr | | | Cotton[1]/ Lima Bean | | | Soybean | | | Velvetlf | | | Wheat | | |
|---|---|---|---|---|---|---|---|---|---|---|---|---|---|---|---|
| Example | PC or V | K | F | PC or V | K | F | PC or V | K | F | PC or V | K | F | PC or V | K | F |
| 1 | 4 | 0 | B | 4 | 0 | DEB | 4 | 0 | ABD | 4 | 0 | B | 4 | 0 | 0 |
| 2 | 4 | 0 | B | 4 | 0 | ABD | 4 | 0 | ABD | 4 | 0 | AB | 5 | 0 | 0 |
| 3 | 4 | 0 | C | 4 | 0 | C | 4 | 0 | C | 4 | 0 | BCI | 4 | 0 | C |
| 4 | 4 | 0 | A | 5 | 0 | 0 | 5 | 0 | 0 | 4 | 0 | A | 4 | 0 | A |
| 5 | 5 | 0 | 0 | 5 | 0 | 0 | 5 | 0 | 0 | 5 | 0 | 0 | 5 | 0 | 0 |
| 6 | | | | | | | | | | | | | | | |
| 7 | 4 | 0 | C | 4 | 0 | CDM | 3 | 0 | CDIM | 3 | 0 | CE | 3 | 0 | C |
| 8 | 4 | 0 | AM | 3 | 0 | AEM | 3 | 0 | ABD | 3 | 0 | E | 4 | 0 | E |
| 9 | 4 | 0 | C | 4 | 20 | CI | 4 | 0 | CIM | 4 | 90 | C | 4 | 0 | C |
| 10 | 5 | 0 | 0 | 4 | 0 | A | 4 | 0 | A | 4 | 0 | AB | 5 | 0 | 0 |
| 11 | 4 | 0 | C | 3 | 0 | CM | 4 | 0 | CEIM | 0 | 100 | 0 | 4 | 0 | CM |
| 12 | 5 | 0 | 0 | 5 | 0 | 0 | 4 | 0 | C | 5 | 0 | 0 | 4 | 0 | C |
| 13 | 4 | 0 | A | 5 | 0 | 0 | 5 | 0 | 0 | 5 | 0 | 0 | 4 | 0 | A |
| 14 | 4 | 0 | C | 4 | 30 | CI | 3 | 0 | BCDI | 4 | 20 | C | 4 | 0 | C |
| 15 | 3 | 10 | A | 3 | 0 | ABDE | 3 | 0 | ABD | 4 | 0 | AB | 3 | 0 | A |
| 16 | 4 | 0 | A | 3 | 0 | ABD | 4 | 0 | ABD | 3 | 20 | BE | 4 | 0 | A |
| 17 | 4 | 0 | A | 2 | 0 | BED | 3 | 0 | ABD | 2 | 20 | ABE | 4 | 0 | A |
| 18 | 4 | 10 | C | 3 | 0 | BCE | 3 | 0 | BCDEP | 3 | 0 | E | 4 | 0 | BC |
| 19 | 3 | 0 | BCE | 2 | 0 | BCE | 3 | 0 | BCD | 3 | 90 | BCE | 3 | 0 | BC |
| 20 | 3 | 20 | C | 2 | 30 | BCM | 2 | 0 | BCDE | 3 | 40 | BCE | 4 | 0 | M |
| 21 | 4 | 0 | BCE | 2 | 50 | BCM | 2 | 0 | BCDM | 2 | 90 | BCE | 4 | 0 | CEM |
| 22 | 4 | 0 | A | 3 | 0 | H | 3 | 0 | ABDE | 3 | 0 | AE | 5 | 0 | 0 |
| 23 | 3 | 10 | BCE | 0 | 100 | 0 | 2 | 30 | BCDM | 0 | 100 | 0 | 3 | 0 | CE |
| 24 | 3 | 10 | CE | 3 | 0 | CE | 3 | 0 | BCD | 3 | 0 | BCE | 5 | 0 | 0 |
| 25 | 4 | 0 | PM | 3 | 0 | B3E | 3 | 0 | BAP | 4 | 0 | B1E | 4 | 0 | B1E |
| 26 | 5 | 0 | 0 | 5 | 0 | 0 | 3 | 0 | DEC3 | 5 | 0 | 0 | 5 | 0 | 0 |
| 27 | 40 | | E | 40 | | E | 50 | | B5EID | 50 | | BE | 20 | | E |
| 28 | 20 | | AB1M | 80 | | AB2H3 | 10 | | AB3DP | 60 | | AB2E | 10 | | A |
| 29 | 40 | | AB3 | 30 | | AE | 50 | | AB3DE | 30 | | E | 10 | | I |
| 30 | 50 | | L | 30 | | AB4 | 30 | | AB5I | 40 | | AE | 50 | | AN |
| 31 | 0 | | 0 | 0 | | 0 | 40 | | B5ED | 0 | | 0 | 30 | | AB1 |
| 32 | 4 | 20 | AM | 2 | 0 | BEM | 3 | 0 | BDIM | 3 | 0 | BEM | 4 | 0 | AM |
| 33 | 4 | 0 | CE | 3 | 0 | BEM | 2 | 0 | BCD | 3 | 0 | BCEI | 3 | 0 | BCEM |
| 34 | 3 | 0 | A | 4 | 0 | AD | 4 | 0 | AM | 2 | 90 | BM | 3 | 0 | AM |
| 35 | 4 | 0 | A | 4 | 0 | A | 4 | 0 | A | 3 | 0 | AB | 4 | 0 | A |
| 36 | 5 | 0 | 0 | 3 | 0 | ABD | 3 | 0 | ABD | 3 | 50 | AB | 4 | 0 | A |
| 37 | 4 | 0 | AB | 3 | 0 | ABDE | 4 | 0 | BD | 5 | 0 | 0 | 5 | 0 | 0 |
| 38 | 4 | 0 | C | 4 | 0 | CI | 4 | 0 | CI | 4 | 0 | C | 4 | 0 | C |
| 39 | 4 | 0 | A | 4 | 0 | A | 4 | 0 | I | 4 | 10 | A | 4 | 0 | A |
| 40 | 4 | 30 | AB | 4 | 0 | BDI | 4 | 0 | ADI | 4 | 0 | A | 5 | 0 | 0 |
| 41 | 3 | 50 | AB | 4 | 0 | AI | 4 | 0 | A | 4 | 0 | B | 5 | 0 | 0 |
| 42 | 4 | 0 | C | 4 | 0 | CPM | 3 | 0 | BCDI | 4 | 0 | C | 3 | 0 | C |
| 43 | 0 | 100 | 0 | 4 | 0 | A | 4 | 0 | ADI | 5 | 0 | 0 | 4 | 0 | A |
| 44 | 4 | 0 | AB | 4 | 0 | AI | 4 | 50 | BI | 4 | 0 | AI | 3 | 0 | C |

TABLE II-continued

| Postemergence Tests Plant | | | | | | | | | | | | | | | |
|---|---|---|---|---|---|---|---|---|---|---|---|---|---|---|---|
| 45 | 3 | 30 | A | 4 | 0 | A | 5 | 0 | 0 | 5 | 0 | 0 | 4 | 0 | A |
| 46 | 5 | 0 | 0 | 5 | 0 | 0 | 4 | 0 | AI | 4 | 0 | I | 4 | 0 | A |
| 47 | 5 | 0 | 0 | 3 | 0 | C | 4 | 0 | CM | 4 | 0 | C | 5 | 0 | 0 |
| 48 | 4 | 0 | A | 4 | 0 | I | 5 | 0 | 0 | 3 | 30 | AB | 4 | 0 | A |
| 49 | 4 | 20 | BCM | 4 | 0 | CIM | 4 | 0 | CDIM | 3 | 30 | C | 4 | 0 | CM |
| 50 | 5 | 0 | 0 | 4 | 0 | A | 4 | 0 | AD | 4 | 0 | A | 4 | 0 | A |
| 51 | 4 | 0 | A | 4 | 0 | BDEI | 3 | 0 | ABD | 3 | 0 | ABE | 4 | 0 | A |
| 52 | 3 | 20 | AB | 2 | 0 | BED | 3 | 0 | BD | 3 | 0 | BE | 4 | 0 | AM |
| 53 | 5 | 0 | 0 | 4 | 0 | A | 4 | 0 | AEI | 4 | 0 | I | 5 | 0 | 0 |
| 54 | 3 | 0 | ABEM | 2 | 0 | BEM | 3 | 0 | ABD | 2 | 0 | BEM | 4 | 0 | AE |
| 55 | 3 | 0 | ABM | 3 | 0 | EM | 2 | 0 | ABD | 3 | 0 | E | 4 | 0 | A |
| 56 | 3 | 0 | BCM | 2 | 0 | BEM | 2 | 0 | BCD | 2 | 30 | BCDI | 4 | 0 | M |
| 57 | 4 | 0 | A | 3 | 0 | H | 3 | 0 | BDEI | 3 | 0 | E | 5 | 0 | 0 |
| 58 | 3 | 20 | BCM | 2 | 0 | BCEI | 3 | 0 | BCD | 0 | 100 | 0 | 3 | 0 | C |
| 59 | 3 | 20 | AB | 3 | 0 | AE | 3 | 0 | ABD | 3 | 70 | ABE | 4 | 0 | A |
| 60 | 4 | 0 | PEM | 3 | 0 | B2E | 4 | 0 | B4P | 4 | 0 | E | 4 | 0 | P |
| 61 | 20 | | B2EP | 20 | | B2E | 60 | | B6PDEM | 10 | | ED1 | 0 | | M |
| 62 | 5 | 0 | 0 | 5 | 0 | 0 | 5 | 0 | 0 | 5 | 0 | 0 | 5 | 0 | 0 |
| 63 | 40 | | E | 40 | | E | 50 | | B6EID | 50 | | BE | 20 | | E |
| 64 | 20 | | AB1 | 20 | | AB1 | 10 | | B2DP | 30 | | AB2E | 30 | | A |
| 65 | 40 | | AB3E | 20 | | E | 50 | | AB3DE | 30 | | E | 10 | | I |
| 66 | 0 | | 0 | 0 | | 0 | 40 | | B5ED | 10 | | BE | 0 | | 0 |
| 67 | 0 | | 0 | 0 | | 0 | 40 | | AB2DEIP | 0 | | 0 | 20 | | E |
| 68 | 4 | 0 | AM | 4 | 0 | BDE | 4 | 0 | ABD | 3 | 0 | ABE | 4 | 0 | A |
| 69 | 4 | 0 | A | 5 | 0 | 0 | 3 | 0 | ABDI | 4 | 0 | A | 5 | 0 | 0 |
| 70 | 4 | 0 | A | 5 | 0 | 0 | 4 | 0 | A | 4 | 0 | I | 2 | 0 | A |
| 71 | 4 | 0 | C | 4 | 0 | C | 4 | 0 | C | 5 | 0 | 0 | 5 | 0 | 0 |
| 72 | 5 | 0 | 0 | 4 | 0 | ABD | 4 | 0 | ABD | 4 | 0 | BE | 5 | 0 | 0 |
| 73 | 3 | 30 | BC | 4 | 0 | BCD | 4 | 0 | BCD | 3 | 0 | BC | 4 | 0 | C |
| 74 | 4 | 20 | C | 4 | 0 | CD | 4 | 0 | CDI | 3 | 40 | BC | 4 | 0 | C |
| 75 | 4 | 0 | A | 5 | 0 | 0 | 4 | 0 | A | 4 | 0 | A | 4 | 0 | A |
| 76 | 4 | 0 | M | 5 | 0 | 0 | 4 | 0 | M | 3 | 70 | AM | 4 | 0 | M |
| 77 | 4 | 0 | C | 4 | 0 | CM | 4 | 0 | CDIM | 3 | 30 | BCM | 3 | 0 | M |
| 78 | 4 | 0 | CM | 4 | 0 | CD | 4 | 0 | BCDM | 3 | 0 | CE | 4 | 0 | C |
| 79 | 3 | 0 | ABE | 4 | 0 | AEM | 3 | 0 | ABD | 3 | 0 | EN | 4 | 0 | AEM |
| 80 | 5 | 0 | 0 | 4 | 0 | C | 4 | 0 | C | 3 | 30 | BC | 4 | 0 | C |
| 81 | 4 | 20 | A | 5 | 0 | 0 | 5 | 0 | 0 | 5 | 0 | 0 | 5 | 0 | 0 |
| 82 | 4 | 20 | A | 4 | 0 | D | 4 | 0 | ADI | 4 | 0 | ABE | 5 | 0 | 0 |
| 83 | 3 | 0 | AB | 3 | 0 | ABD | 3 | 0 | ABD | 3 | 0 | ABE | 4 | 0 | A |
| 84 | 4 | 0 | A | 3 | 0 | BDEI | 4 | 0 | D | 3 | 0 | AEI | 4 | 0 | A |
| 85 | 3 | 0 | BCE | 2 | 0 | BE | 3 | 0 | BCD | 2 | 0 | BCE | 3 | 0 | CE |
| 86 | 3 | 20 | BCM | 3 | 40 | BCI | 3 | 30 | BCD | 2 | 50 | BCE | 4 | 0 | M |
| 87 | 4 | 0 | C | 3 | 0 | BEH | 3 | 0 | BCDEIP | 3 | 0 | BCE | 4 | 0 | C |
| 88 | 3 | 10 | BC | 0 | 100 | 0 | 2 | 20 | BCD | 0 | 100 | 0 | 4 | 0 | C |
| 89 | 3 | 0 | BC | 3 | 0 | CE | 3 | 0 | BCD | 2 | 0 | BCE | 4 | 0 | C |
| 90 | 5 | 0 | 0 | 3 | 0 | B4H | 4 | 0 | B4M | 3 | 0 | B1E | 4 | 0 | E |
| 91 | 3 | 0 | M | 3 | 0 | E | 3 | 0 | B4M | | | | 4 | 0 | MI |
| 92 | 20 | | C1M | 30 | | B2C1 | 40 | | B3C2DEP | 30 | | B2C1E | 20 | | C1 |
| 93 | 20 | | AM | 30 | | AB2 | 20 | | AB4DP | 70 | | AB2E | 20 | | A |
| 94 | 0 | | 0 | 30 | | AE | 50 | | AB3DEP | 30 | | E | 10 | | AE |
| 95 | 3 | 20 | AM | 4 | 0 | AM | 4 | 0 | ADM | 2 | 80 | ABI | 3 | 0 | A |
| 96 | 5 | 0 | 0 | 4 | 0 | A | 5 | 0 | 0 | 3 | 0 | AB | 5 | 0 | 0 |
| 97 | 10 | | A | 70 | 0 | B3EAH2 | 50 | | B3AE | 10 | | E | 0 | | 0 |
| 98 | 60 | | AB3EPU | 90 | | AB4U | 20 | | AB5DPU | 10 | | AB3EM | 50 | | AB1EM |
| 99 | 10 | | ME | 10 | | E | 10 | | PDIAE | 20 | | B1EM | 10 | | M |
| 100 | 20 | | AB1M | 30 | | E[1] | 20 | | B1D | 30 | | E | 20 | | A |
| 101 | 40 | | AB3 | 40 | | AE[1] | 50 | | B5DE | 30 | | E | 40 | | A |
| 102 | 0 | | 0 | 0 | | 0[1] | 0 | | 0 | 0 | | 0 | 0 | | 0 |
| 103 | 0 | | 0 | 0 | | 0[1] | 0 | | 0 | 0 | | 0 | 0 | | 0 |
| 104 | 10 | | A | 0 | | 0[1] | 10 | | AB1 | 20 | | B2E | 20 | | A |
| 105 | 60 | | L | 70 | | H1[1] | 50 | | EFMB5P | 100 | | 0 | 10 | | I |
| 106 | 10 | | B3 | 50 | | H3B5[1] | 40 | | B5EUPD | 40 | | BE | 10 | | B1 |
| 107 | 30 | | AB1M | 40 | | AB1IM[1] | 60 | | B3I | 20 | | BE | 10 | | 0 |
| 108 | 40 | | B2E | 30 | | B1EI | 40 | | AB3DEM | 60 | | BEI | 10 | | EM |

FOOTNOTES
The footnotes in Table I are also applicable in Table II.

What is claimed is:

1. Plant growth and development modifying 2-(2-oxycarbonylphenyl)benzoxazoles of the formula

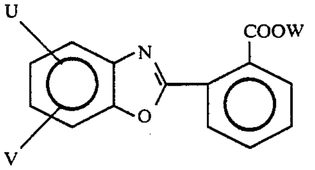

wherein

U is —OZ, and Z is selected from -phenyl; -phenyl carrying 1 or 2 substituents independently selected from -halogen, -lower haloalkyl, and -acetamido; -naphthyl;

V is -hydrogen; and

W is selected from -hydrogen, -lower alkyl and an agriculturally acceptable cation.

2. A compound of claim 1 selected from agriculturally acceptable cation salts of 2-(2-carboxyphenyl)-6-(2-chloro-4-trifluoromethylphenoxy)benzoxazole.

3. 2-(2-Carboxyphenyl)-6-(2-chloro-4-trifluoromethylphenoxy)benzoxazole.

4. 2-(2-Carboxyphenyl)-5-phenoxybenzoxazole.

5. A plant growth and development modifying composition comprising in admixture with an agriculturally acceptable carrier a plant growth and development modifying effective amount of 2-(2-carboxyphenyl)-6-(2-chloro-4-trifluoromethylphenoxy)benzoxazole.

6. A plant growth and development modifying composition comprising in admixture with an agriculturally acceptable carrier a plant growth and development modifying effective amount of 2-(2-carboxyphenyl)-5-phenoxybenzoxazole.

7. A plant growth and development modifying composition comprising in admixture with an agriculturally acceptable carrier an agriculturally acceptable cation salt of 2-(2-carboxyphenyl)-6-(2-chloro-4-trifluoromethylphenoxy)benzoxazole.

8. A method of modifying the growth and development of plants which comprises applying to the locus where such modification is desired a plant growth and development modifying effective amount of at least one 2-(2-oxycarbonylphenyl)benzoxazole of the formula

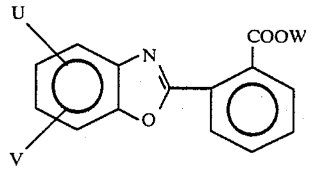

wherein

U is selected from -hydrogen, -lower alkyl, -lower alkenyl, -phenylmethyl, -phenyl, -phenylcarbonyl, -halophenylcarbonyl, -phenylthio, -phenylsulfoxy, -phenylsulfonyl, and —OZ in which Z is -aryl or -aryl carrying 1 or 2 substituents independently selected from -halogen, -lower alkyl, -lower haloalkyl, -lower alkoxy, -acetamido, and -phenyl; wherein aryl denotes phenyl or naphthyl;

V is selected from -hydrogen, -lower alkyl, or U and V taken together are —$C_4H_4$— joining adjacent ring positions, with the proviso that V is not -hydrogen or -lower alkyl unless U is other than -hydrogen and -lower alkyl; and W is selected from -hydrogen, -lower alkyl and an agriculturally acceptable cation.

9. A method according to claim 8 wherein said 2-(2-oxycarbonylphenyl)benzoxazole is selected from 2-(2-carboxyphenyl)-6-phenoxybenzoxazole; 2-(2-carboxyphenyl)-6-(4-chlorophenoxy)benzoxazole; 2-(2-carboxyphenyl)-6-(2,4-dichlorophenoxy)benzoxazole; 2-(2-carboxyphenyl)-6-(2-chloro-4-trifluoromethylphenoxy)benzoxazole; 2-(2-carboxyphenyl)-6-phenylbenzoxazole; 2-(2-carboxyphenyl)-5-phenoxybenzoxazole; 2-(2-carboxyphenyl)-6-(4-methylphenoxy)benzoxazole; 2-(2-carboxyphenyl)-6-(phenylsulfinyl)benzoxazole; 2-(2-carboxyphenyl)-6-(4-acetamidophenoxy)benzoxazole; 2-(2-carboxyphenyl)-6-(2,2-dimethyl-7-benzofuranoxy)benzoxazole; 2-(2-carboxyphenyl)-naphtho[2,1-]oxazole; 2-(2-carbomethoxyphenyl)-6-phenoxybenzoxazole; 2-(2-carbomethoxyphenyl)-6-(α-naphthoxy)benzoxazole; and agriculturally acceptable cation salts of 2-(2-carboxyphenyl)-6-(2,4-dichlorophenoxy)-benzoxazole, 2-(2-carboxyphenyl)-6-(2-chloro-4-trifluoromethylphenoxy)benzoxazole, and 2-(2-carboxyphenyl)-6-(4-methylphenoxy)benzoxazole.

10. A method according to claim 8 wherein said 2-(2-carboxyphenyl)benzoxazole is 2-(2-carboxyphenyl)-6-phenylbenzoxazole.

11. A method according to claim 8 wherein said 2-(2-oxycarbonylphenyl)benzoxazole is 2-(2-carboxyphenyl)-6-(2-chloro-4-trifluoromethylphenoxy)benzoxazole.

12. A method according to claim 8 wherein said 2-(2-oxycarbonylphenyl)benzoxazole is 2-(2-carboxyphenyl)-5-phenoxybenzoxazole.

13. A method according to claim 8 wherein said 2-(2-oxycarbonylphenyl)benzoxazole is selected from agriculturally acceptable cation salts of 2-(2-carboxyphenyl)-6-(2-chloro-4-trifluoromethylphenoxy)benzoxazole.

14. A method of controlling the growth of plants which comprises applying to the locus where control is desired a herbically effective amount of at least one 2-(2-oxycarbonylphenyl)benzoxazole selected from 2-(2-carboxyphenyl)-6-phenoxybenzoxazole; 2-(2-carboxyphenyl)-6-(4-chlorophenoxy)benzoxazole; 2-(2-carboxyphenyl)-6-(2,4-dichlorophenoxy)benzoxazole; 2-(2-carboxyphenyl)-6-(2-chloro-4-trifluoromethylphenoxy)benzoxazole; and agriculturally acceptable cation salts of 2-(2-carboxyphenyl)-6-(2,4-dichlorophenoxy)benzoxazole, 2-(2-carboxyphenyl)-6-(2-chloro-4-trifluoromethylphenoxy)benzoxazole, and 2-(2-carboxyphenyl)-6-(4-methylphenoxy)benzoxazole.

15. A method according to claim 14 wherein said 2-(2-oxycarbonylphenyl)benzoxazole is selected from agriculturally acceptable cation salts of 2-(2-carboxyphenyl)-6-(2-chloro-4-trifluoromethylphenoxy)benzoxazole.

16. A method of regulating the growth of plants which comprises applying to the locus where regulation is desired a plant growth regulant effective amount of at least one 2-(2-oxycarbonylphenyl)benzoxazole selected from 2-(2-carboxyphenyl)-6-phenylbenzoxazole; 2-(2-carboxyphenyl)-5-phenoxybenzoxazole; 2-(2-carboxyphenyl)-6-phenoxybenzoxazole; 2-(2-carboxyphenyl)-6-(2-chloro-4-trifluoromethylphenoxy)benzoxazole; 2-(2-carboxyphenyl)-6-(4-methylphenoxy)benzoxazole; 2-(2-carboxyphenyl)-6-(phenylsulfinyl)benzoxazole; 2-(2-carboxyphenyl)-6-(4-acetamidophenoxy)benzoxazole; 2-(2-carboxyphenyl)-6-(2,2-dimethyl-7-benzofuranoxy)-benzoxazole; 2-(2-carboxyphenyl)-naphtho[2,1-d]-oxazole; 2-(2-carbomethoxyphenyl)-6-phenoxybenzoxazole; 2-(2-carbomethoxyphenyl)-6-(α-naphthoxy)benzoxazole; and agriculturally acceptable cation salts of 2-(2-carboxyphenyl)-6-(2-chloro-4-trifluoromethylphenoxy)benzoxazole.

17. A method according to claim 16 wherein said 2-(2-oxycarbonylphenyl)benzoxazole is selected from 2-(2-carboxyphenyl)-6-phenylbenzoxazole, 2-(2-carboxyphenyl)-6-(2-chloro-4-trifluoromethylphenoxy)benzoxazole, and 2-(2-carboxyphenyl)-5-phenoxybenzoxazole.

18. A method according to claim 16 wherein said 2-(2-oxycarbonylphenyl)benzoxazole is 2-(2-carboxyphenyl)-5-phenoxybenzoxazole.

* * * * *

UNITED STATES PATENT AND TRADEMARK OFFICE
CERTIFICATE OF CORRECTION

PATENT NO. : 4,659,360

DATED : April 21, 1987

INVENTOR(S) : Jonathan S. Baum and Tsong M. Chen

It is certified that error appears in the above-identified patent and that said Letters Patent is hereby corrected as shown below:

In the ABSTRACT, first line after the formula "-OZ", "carring" should read --carrying--. Column 5, Example 27, "-2-(2-Carboxyphenyl)-6-(αnaphthoxy)" should read --2-(2-Carboxyphenyl)-6-(α-naphthoxy)--. Column 5, Example 28, 2-(2-Carboxyphenyl)-6-(βnaphthoxy)" should read --2-(2-Carboxyphenyl)-6-(β-naphthoxy)--. Column 7, Example 103, "[2-(1-ethoxypropanoyl)" should read --2-(Carbo-[2-(1-ethoxypropanoyl)--. Column 7, line 43, "employed free from" should read --be employed free from--. Column 10, line 33, "merged test plants" should read --emerged test plants--. Column 12, line 5 "increased chlorophyll product" should read --increased chlorophyll production--. Column 13, Table I, Example 18,under heading Barngr. PC or V K F, "ABNE" should read ABEN--. Column 13, Table I, Example 27, under heading Corn-F PC or V K F, "BEM" should read --B3M--. Column 15, Table I, Example 65, under heading Bindweed PC or V K F, "BE1" should read --B1E--.

Signed and Sealed this

Sixteenth Day of February, 1988

Attest:

DONALD J. QUIGG

Attesting Officer

Commissioner of Patents and Trademarks